(12) United States Patent
Masilamani et al.

(10) Patent No.: US 7,869,033 B2
(45) Date of Patent: Jan. 11, 2011

(54) CANCER DETECTION BY OPTICAL ANALYSIS OF BODY FLUIDS

(76) Inventors: Vadivel Masilamani, P.O. Box 2455, Riyadh, 11451 (SA); Masilamani Elangovan, 3287 Kincross Cir., Herndon, VA (US) 20171

( * ) Notice: Subject to any disclaimer, the term of this patent is extended or adjusted under 35 U.S.C. 154(b) by 244 days.

(21) Appl. No.: 12/285,670

(22) Filed: Oct. 10, 2008

(65) Prior Publication Data
US 2009/0046286 A1   Feb. 19, 2009

Related U.S. Application Data

(63) Continuation-in-part of application No. 12/000,233, filed on Dec. 11, 2007, now abandoned, which is a continuation-in-part of application No. 11/017,913, filed on Dec. 22, 2004, now abandoned.

(60) Provisional application No. 60/531,987, filed on Dec. 24, 2003.

(51) Int. Cl.
    *G01N 21/64* (2006.01)
(52) U.S. Cl. .................. 356/317; 356/39; 356/318; 250/459.1
(58) Field of Classification Search ............ 356/39, 356/317, 318, 417; 250/458.1, 459.1
    See application file for complete search history.

(56) References Cited

U.S. PATENT DOCUMENTS

| | | |
|---|---|---|
| 4,541,438 A | 9/1985 | Parker et al. |
| 4,933,274 A | 6/1990 | Sanford et al. |
| 5,131,398 A | 7/1992 | Alfano et al. |
| 5,270,171 A | 12/1993 | Cercek et al. |
| 5,422,093 A | 6/1995 | Kennedy et al. |
| 5,579,773 A | 12/1996 | Vo-Dinh et al. |
| 6,083,487 A | 7/2000 | Biel |
| 6,091,985 A | 7/2000 | Alfano et al. |
| 6,256,530 B1 | 7/2001 | Wolfe |
| 6,316,215 B1 | 11/2001 | Adair et al. |
| 6,696,241 B2 | 2/2004 | Thompson et al. |
| 6,750,037 B2 | 6/2004 | Adair et al. |
| 6,984,498 B2 | 1/2006 | Adair |
| 2002/0115121 A1 | 8/2002 | Garwin |
| 2004/0202612 A1 | 10/2004 | Adair |

OTHER PUBLICATIONS

Rabinowitz, Cancer Research, A Correlation of Fluorescence of Human Urine with Benign and Malignant Growth, vol. 9, No. 11, Nov. 1949, pp. 672-676.*

Madhuri et al, Proc. SPIE, Ultraviolet Fluorescence Spectroscopy of Blood Plasma in the Discrimination of Cancer from Normal, vol. 2982, 1997, pp. 41-45.*

Karthikeyan et al, Pathology Oncology Research, Spectrofluorimetric Detection of DMBA-Induced Mouse Skin Carcinoma, vol. 5, No. 1, 1999, pp. 46-48.*

Madhuri et al, Photochemistry and Photobiology, Native Fluorescence Spectroscopy of Blood Plasma in the Characterization of Oral Malignancy, vol. 78, No. 2, Aug. 2003, pp. 197-204.*

* cited by examiner

*Primary Examiner*—F. L Evans
(74) *Attorney, Agent, or Firm*—Richard C. Litman

(57) ABSTRACT

The optical analysis of body fluids is a method of determining the relative concentration of certain bio-molecules in blood and urine samples by fluorescent spectroscopy. The relative concentration of these bio-molecules serves as a marker or screening test to assess the presence and stage of cancer in some organ or tissue of the body, and in some cases, the presence of particular types of cancer in the body. The bio-molecules include various species of porphyrin, flavins (including flavin mononucleotide[FMN], flavin adeno dinucleotide [FAD], and riboflavin), bile components (including biliverdin and bilirubin), tyrosine, tryptophan, and NAD(P)H. The fluorescent spectroscopy techniques include determining intensity maxima in the emission spectra at particular excitation wavelengths characteristic of the bio-molecules, determining intensity maxima in the excitation spectra at particular emission wavelengths characteristic of the bio-molecules, and synchronous scanning of the excitation and emission spectra while maintaining particular offsets in the wavelengths.

20 Claims, 23 Drawing Sheets

CANCER DETECTION BY OPTICAL ANALYSIS OF BODY FLUIDS

CROSS-REFERENCE TO RELATED APPLICATIONS

This application is a continuation-in-part of U.S. patent application Ser. No. 12/000,233, filed Dec. 11, 2007 now abandoned, the contents of which are hereby incorporated by reference in their entirety and which is a continuation-in-part of U.S. patent application Ser. No. 11/017,913, filed Dec. 22, 2004, now abandoned, which claims priority to U.S. provisional patent application 60/531,987, filed Dec. 24, 2003. This application also claims priority to India patent application number 587/CHE/2003, filed Jul. 22, 2003 and issued as India patent number 209084 on Aug. 20, 2007.

BACKGROUND OF THE INVENTION

1. Field of the Invention

The present invention relates to the diagnosis of cancer, and particularly to the optical analysis of body fluids, such as blood or urine, by fluorescent spectroscopy in order to detect the presence of cancer and the relative severity or stage of the disease both as a diagnostic screening method and for evaluating the progress of treatment.

2. Description of the Related Art

Cancer is often a fatal disease. Modern medicine has developed many modes of treating cancer, including surgical removal of tumors, chemotherapy, immunological therapy, etc. However, the key to effective treatment is early detection.

A number of diagnostic tests are available for determining the presence of cancer. These tests include: surgical biopsy; protein sequence analysis (PSA); DRE tests; computed axial tomography (CAT or CT scans); magnetic resonance imaging (MRI) scans; ultrasound scans; bone scans; positron emission tomography (PET) scans; bone marrow testing; barium swallow tests; endoscopy; cytoscopy; T/Tn antigen tests; mammography; and other tests. Although effective to a greater or lesser extent, each of these tests has advantages and disadvantages.

Some tests, such as PSA, pap smears, and mammography, are specific to particular organs. Others, such as biopsy, endoscopy, bone marrow, and cytoscopy, are invasive tests that often result in considerable discomfort to the patient. Still others, such as CAT scans and MRI scans, are quite expensive and require complex instrumentation.

There is a need for a simple, relatively inexpensive, non-invasive method of screening patients for the presence of cancer, regardless of the location of the cancer or the affected organ, that can be used both for preliminary diagnosis or mass screening of patients, and also during treatment to determine whether cancer has gone into remission. Thus, an optical analysis of body fluids solving the aforementioned problems is desired.

SUMMARY OF THE INVENTION

The optical analysis of body fluids is a method of determining the relative concentration of certain bio-molecules in blood and urine samples by fluorescent spectroscopy. The relative concentration of these bio-molecules serves as a marker or screening test to assess the presence and stage of cancer in some organ or tissue of the body, and in some cases, the presence of particular types of cancer in the body. The bio-molecules include various species of porphyrin, flavins (including flavin mononucleotide [FMN], flavin adeno dinucleotide [FAD], and riboflavin), bile components (including biliverdin and bilirubin), tyrosine, tryptophan, and NAD(P)H. The fluorescent spectrography techniques include determining intensity maxima in the emission spectra at particular excitation wavelengths characteristic of the bio-molecules, determining intensity maxima in the excitation spectra at particular emission wavelengths characteristic of the bio-molecules, and synchronous scanning of the excitation and emission spectra while maintaining particular offsets in the wavelengths. The method is used to detect the presence of cancer and the relative severity or stage of the disease both as a diagnostic screening method and for evaluating the progress of treatment.

The blood samples may be extracts from blood cells or plasma samples. The urine samples may be fresh urine samples, or extracts from urine. The apparatus used may use either an incoherent light source, such as a lamp, or a coherent light source, such as a laser. The excitation wavelength may be determined by an interference filter, a notch filter, or a grating. The emission intensity may be detected by a photodiode, photomultiplier tube, or CCD array.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
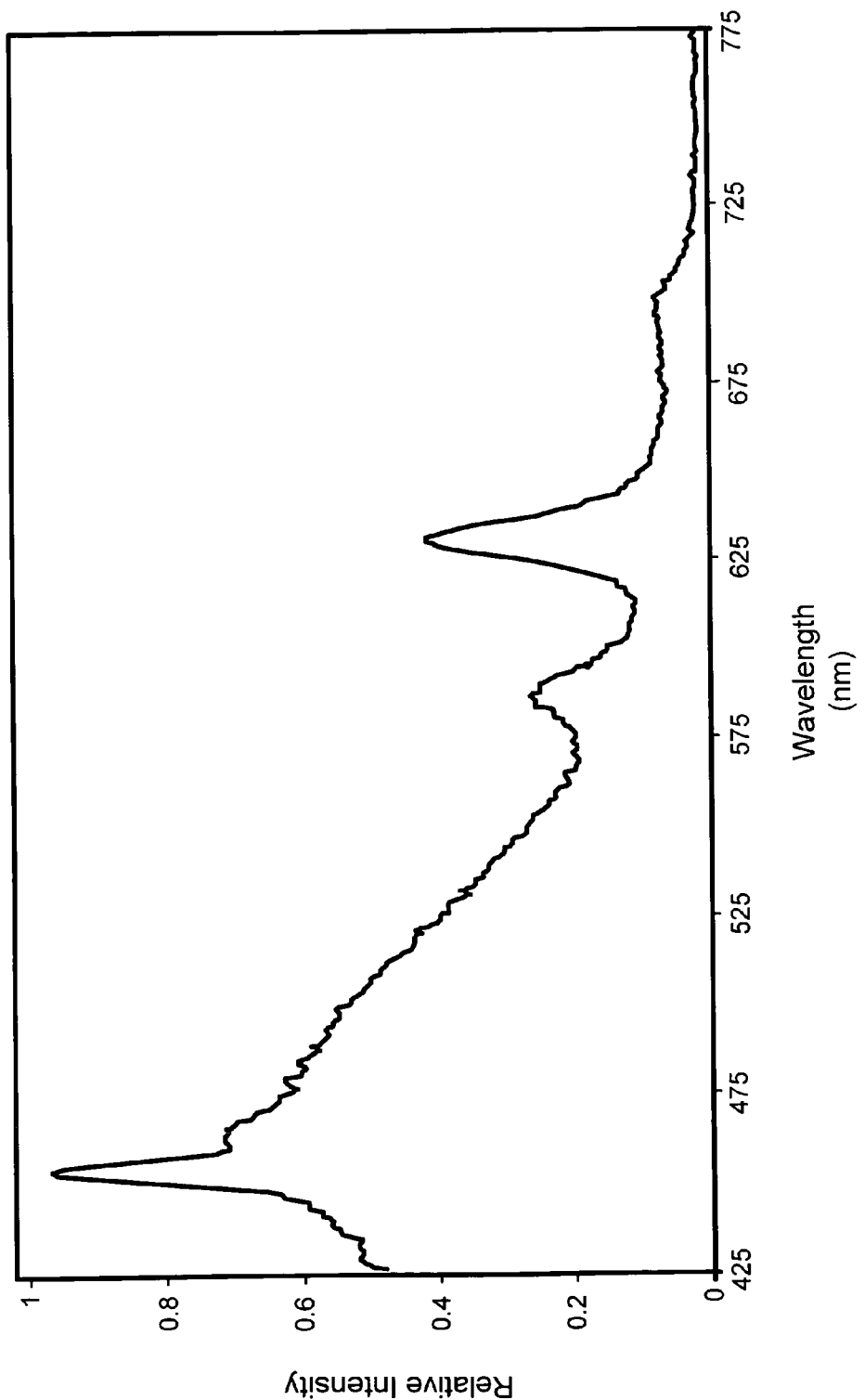
FIG. 1 shows the fluorescence emission spectrum at an excitation wavelength of 400 nm of a sample extract of the formed elements (mostly blood cells) from the blood of a healthy human patient.
Figure 2:
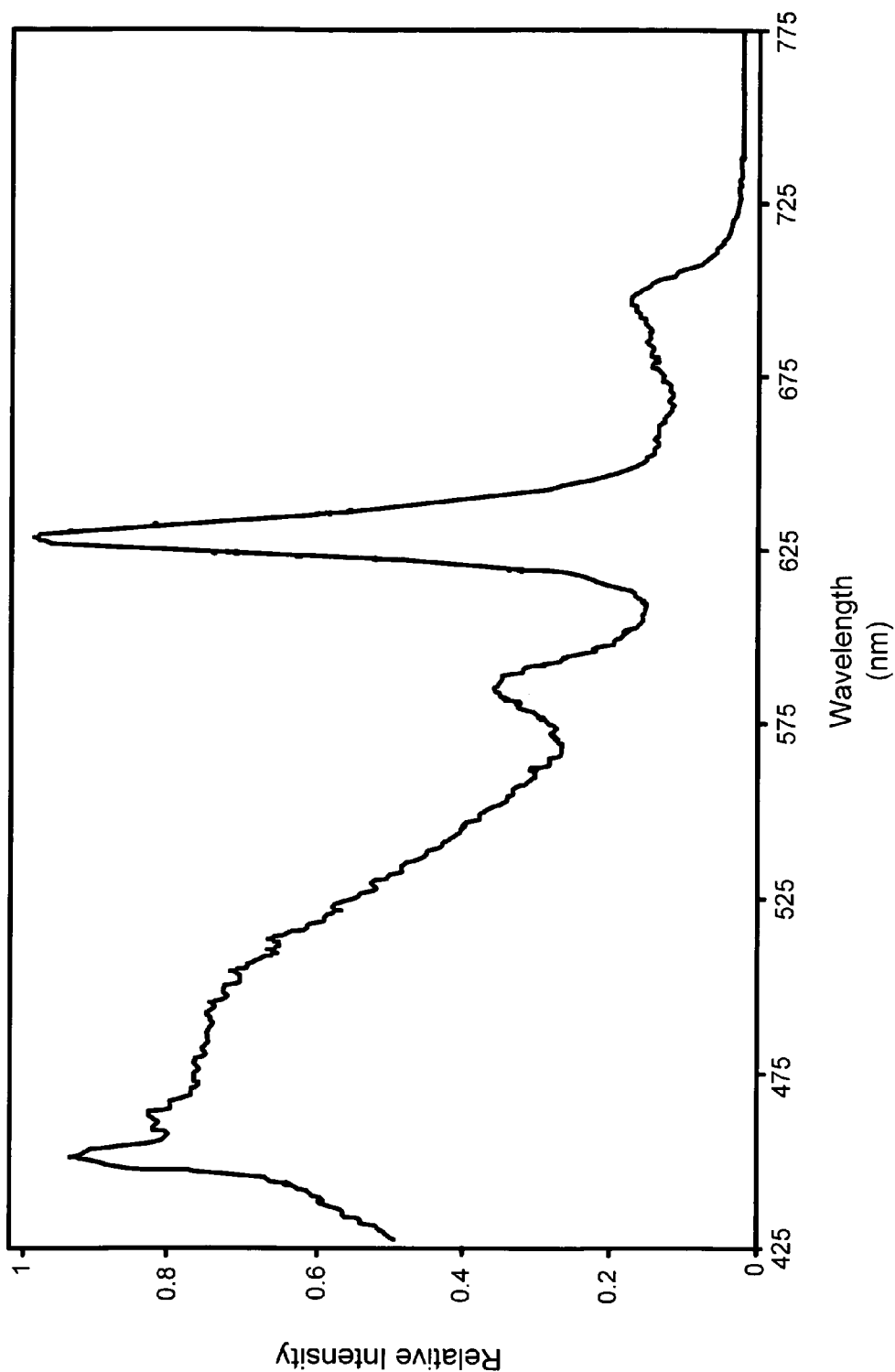
FIG. 2 shows the fluorescence emission spectrum at an excitation wavelength of 400 nm of a sample extract of the formed elements (mostly blood cells) from the blood of a human patient afflicted with cancer.

The optical analysis of body fluids is a method of determining the relative concentration of certain bio-molecules in blood and urine samples by fluorescent spectroscopy. The relative concentration of these bio-molecules serves as a marker or screening test to assess the presence and stage of cancer in some organ or tissue of the body, and in some cases, the presence of particular types of cancer in the body. The bio-molecules include various species of porphyrin, riboflavin, bile components, bilirubin, tryptophan, NAD(P)H, biliverdin, and flavins. The fluorescent spectrography techniques include determining intensity maxima in the emission spectra at particular excitation wavelengths characteristic of the bio-molecules, determining intensity maxima in the excitation spectra at particular emission wavelengths characteristic of the bio-molecules, and synchronous scanning of the excitation and emission spectra while maintaining particular offsets in the wavelengths. The method is used to detect the presence of cancer and the relative severity or stage of the disease both as a diagnostic screening method and for evaluating the progress of treatment.

The method may be carried out using any fluorescent spectrography apparatus known in the art. The optical source may be a lamp, such as a halogen lamp, a mercury lamp, a xenon lamp, a tungsten lamp, or other lamp used in fluorescent spectrographs. Alternatively, the optical source may be a coherent light source, such as a diode laser, a helium-cadmium laser, a frequency-doubled titanium-sapphire laser, or a tunable dye laser. The excitation wavelength may be determined by an interference filter, a notch filter, a slit and grating, or by any other wavelength determining means. Optical detection may be by a photodiode, a photomultiplier tube, an avalanche diode, a CCD array, or any other conventional detector.

Fluorescent spectrography is based upon the phenomenon that certain moles absorb light at certain frequencies or wavelengths to reach an excited energy level, and subsequently decay to a lower energy state by fluorescing at particular wavelengths. Detectors are capable of detecting this fluorescence with great sensitivity, down to parts in a billion, or even from a single molecule.

The optical analysis of body fluids, as set forth herein, rests upon the identification by the present inventors of certain fluorescence excitation-emission wavelengths characteristic of the bio-molecules mentioned above that may be found in body fluids, such as blood and urine. The optical analysis also rests upon the recognition by the present inventors that the relative proportions of such bio-molecules in blood and urine are affected by the presence of cancerous conditions in the body and the stage of development of the cancerous condition. The method will now be explained by reference to particular examples.

Example 1

Human blood samples were prepared as follows. A disposable syringe is used to take 5 ml of venous blood from the subject. The blood was placed in a sterile vial containing ethylene diamide tetraacetic acid (EDTA) anticoagulant. The blood was centrifuged at 4000 rpm for 15 minutes, and the supernatant was separated out and collected in a sterile vial. The residue, which is composed of formed elements containing mostly cellular matter, such as erythrocytes, was treated with acetone in a ratio of 1:2, i.e., 1 ml of formed elements to which 2 ml of acetone was added. This sample was vigorously shaken 100 times and then centrifuged at 4000 rpm for 15 minutes.

The supernatant thus obtained was a clear solution containing the bio-molecules that are tumor markers. A portion of the supernatant was placed in a transparent quartz cuvette and examined in a fluorescent spectrophotometer as follows.

Figure 5:
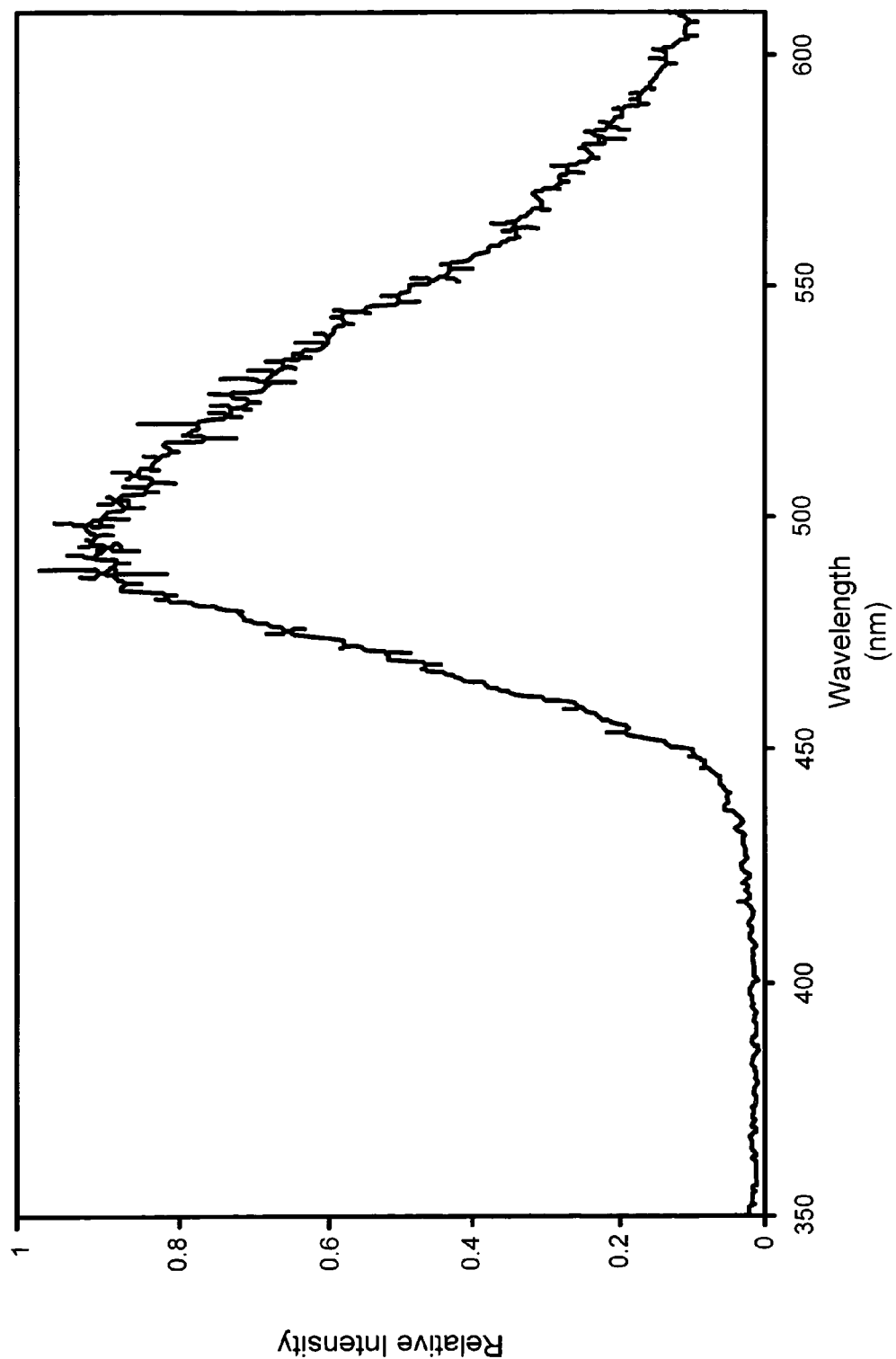
FIG. 5 shows the fluorescence emission spectrum of a urine sample at an excitation wavelength of 325 nm from a human patient afflicted with cancer.
Figure 6:
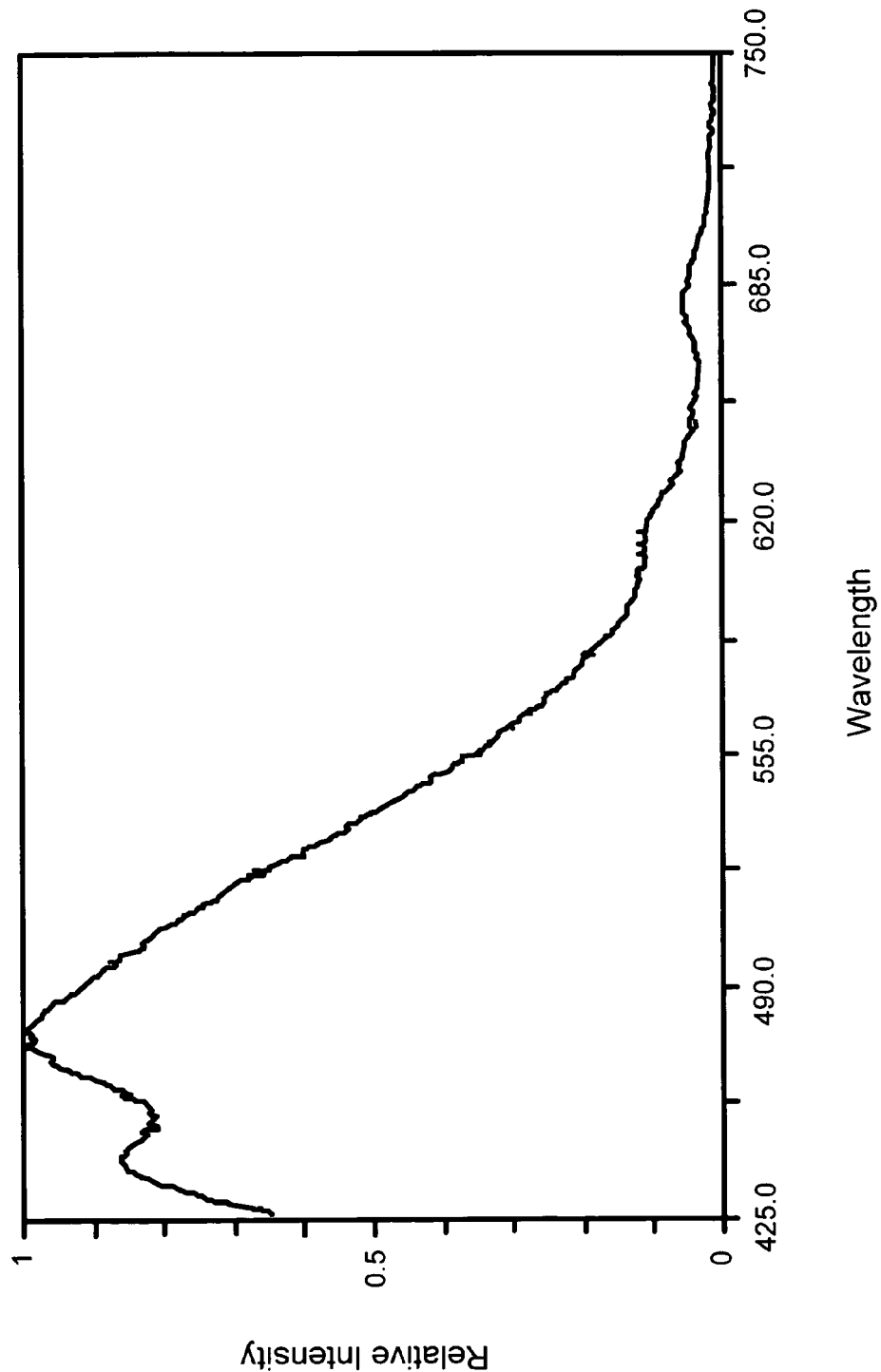
FIG. 6 shows the fluorescence emission spectrum of a urine sample from a healthy human patient at an excitation wavelength of 400 nm.

The excitation wavelength was fixed at 400 nm and the emission spectrum was obtained in the range of 425 nm to 720 nm. FIG. 5 illustrates a representative example of the results for a healthy individual, and FIG. 6 illustrates a representative example of the results for an individual afflicted with cancer. The spectra show a band at around 460 nm, which is due to Raman scattering of the acetone extraction solvent. In addition, the spectra show: (1) a fluorescence band at around 505 nm, most probably due to flavins (as used herein, the term "flavins" refers to flavins generally, including flavin mononucleotide[FMN], flavin adeno dinucleotide [FAD], and riboflavin) or bile components (as used herein, the term "bile components" refers to bile components generally, including biliverdin and bilirubin); (2) a fluorescence band at around 585 nm due to anionic species of porphyrin; (3) a fluorescence band at around 630 nm due to neutral species of porphyrin; and (4) a fluorescence band at around 695 nm due to cationic species of porphyrin. The intensities of emission at these bands were measured and denoted as $I_{460}$, $I_{505}$, $I_{585}$, $I_{630}$, and $I_{695}$.

There are five ratios of these fluorescence intensities of interest. They are:

$R_1 = I_{630}/I_{585}$ = neutral porphyrin/anionic porphyrin $R_2 = I_{695}/I_{585}$ = cationic porphyrin/neutral porphyrin $R_3 = I_{630}/I_{505}$ = neutral porphyrin/riboflavin or bile $R_4 = I_{585}/I_{460}$ = anionic porphyrin/acetone $R_5 = I_{505}/I_{460}$ = riboflavin or bile/acetone These fluorescent intensity ratio parameters are proportional to the ratio of concentration of the above-cited bio-molecules. The ratios are different for healthy and cancerous samples.

For example, if $R_1 < 1.5$, the ratio implies that the patient is healthy. If $1.5 < R_1 < 2.25$, the ratio implies the patient is at high risk for cancer. If $2.25 < R_1 < 3$, the ratio implies that the patient is in the early stages of cancer. If $R_1 > 3$, the ratio implies that the patient is in the advanced stages of cancer. A complete summary of the significance of all five ratios is summarized in Table 1.

TABLE I

Fluorescence Intensity Ratio for Formed Elements

| Ratio | Healthy | High Risk | Early Cancer | Advanced Cancer | Contrast Param. |
|---|---|---|---|---|---|
| $R_1$ | <1.5 | >1.5 <2.25 | >2.25 <3.0 | >3.0 | 2 |
| $R_2$ | 0.4 ± 0.1 | 0.5 ± 0.1 | 0.8 ± 0.2 | 1.5 ± 0.5 | 4 |
| $R_3$ | 0.6 ± 0.2 | 1 ± 0.25 | 1.25 ± 0.25 | 2 ± 0.5 | 3 |
| $R_4$ | 0.3 ± 0.1 | 0.5 ± 0.1 | 0.7 ± 0.1 | 1 ± 0.2 | 3.3 |
| $R_5$ | 0.5 ± 0.1 | 0.7 ± 0.1 | 0.9 ± 0.1 | 1.2 ± 0.2 | 2.2 |

$R_1$, $R_2$, and $R_3$ are common for all types of cancer, since these ratios depend upon the concentration of porphyrin, a bio-molecule involved in heme metabolism. Porphyrin is found at higher concentration in cancer patients than in healthy subjects because of the abnormal cell proliferation in cancer patients. Elevated levels of porphyrin are, in general, the basis for laser-based photodynamic therapy, which is practiced throughout the world.

In the optical analysis of body fluids, the concern is with the concentration of porphyrin carried in the blood stream and excreted in urine. If the concentration of this fluorophore is high, then tumor activity or tumor volume is also high.

These ratio also exhibit some special cases. For example, if $R_4 < 0.5$, the patient is healthy. However, if $0.5 < R_4 < 1.5$, then $R_4$ implies an early stage of Hodgkin's lymphoma. In addition, if $R_5 < 0.5$, the patient is healthy, but if $0.5 < R_5 < 0.75$, mild liver malfunction is indicated, and $0.75 < R_5 < 1.0$ implies severe liver malfunction. These characteristics of $R_5$ are distinct in pancreatic cancer with obstruction of the liver.

Figure 3A:
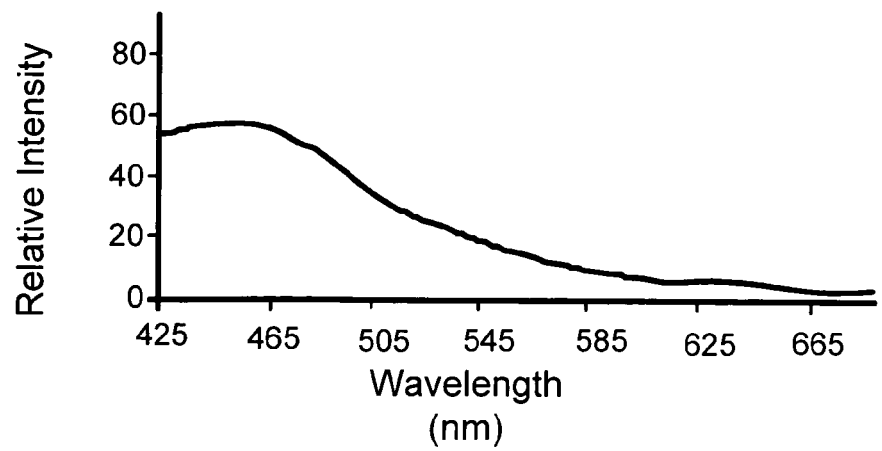
FIG. 3A shows the fluorescence emission spectrum of a sample extract of the formed elements (mostly blood cells) from the blood of a healthy animal (albino mice).
Figure 3B:
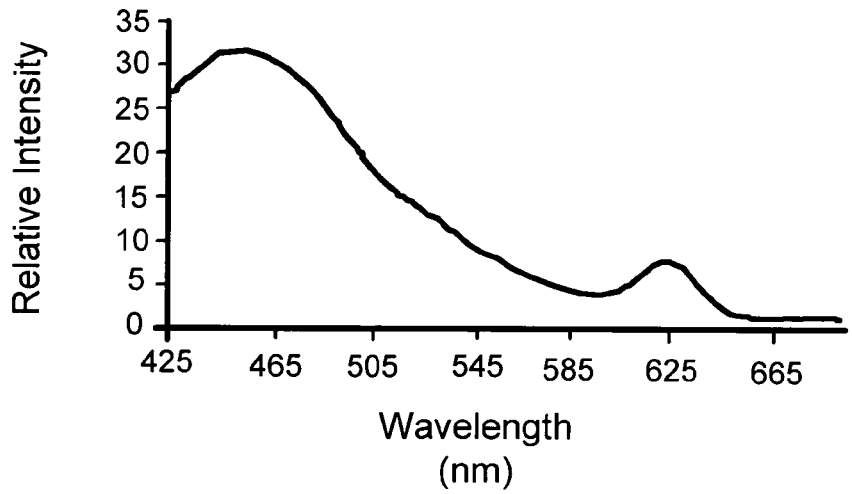
FIG. 3B shows the fluorescence emission spectrum of a sample extract of the formed elements (mostly blood cells) from the blood of an animal (albino mice) with early cancer.
Figure 3C:
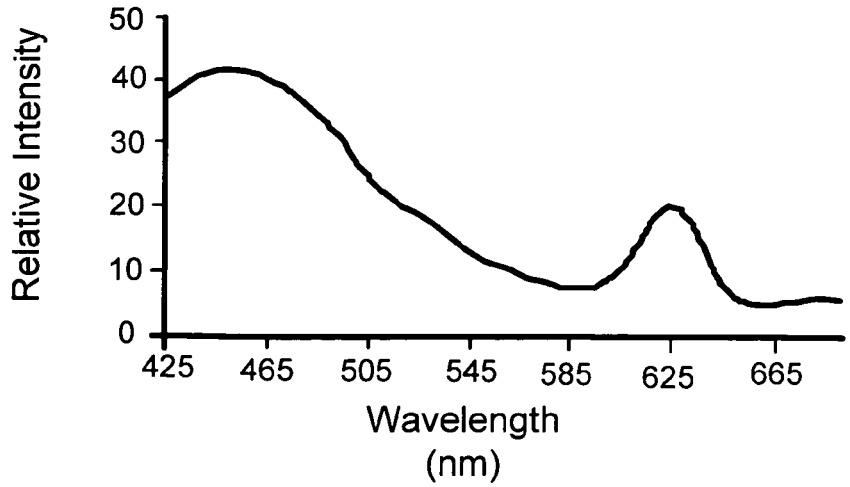
FIG. 3C shows the fluorescence emission spectrum of a sample extract of the formed elements (mostly blood cells) from the blood of an animal (albino mice) with advanced cancer.

The characteristics of the ratios are supported by animal and human studies. One hundred and fifty albino mice were studied in which squamus cell carcinoma had been induced using the chemical carcinogen DMBA. These mice were sacrificed at different stages of cancer, and blood samples taken from the mice were subjected to the sample analysis outlined above. The healthy blood and the cancer-diseased blood showed distinct features. It was seen that $R_1 = I_{630}/I_{585}$ increases as the disease becomes more and more advanced. These results are shown in the exemplary spectra of FIGS. 3A, 3B, and 3C for different stages of cancer development. It will be noted that the 585 nm band is not as distinct as in humans.

Four hundred twenty-four human patients were tested as a field study. The details of the disease and diagnosis score are given in Table II below. The score was done with reference to conventional histopathology.

TABLE II

Testing of Human Subjects

| | | | Correct | Incorrect Diagnosis | |
|---|---|---|---|---|---|
| Item | Type of Subjects | # of Subjects | Optical Diagnosis | False Positive | False Negative |
| 1 | Healthy volunteers | 130 | 123 | 7 | |
| 2 | Cancer of esophagus | 42 | 38 | | 4 |
| 3 | Cancer of Thyroid | 38 | 30 | | 8 |
| 4 | Cancer of Breast | 64 | 60 | | 4 |
| 5 | Hodgkin's Lymphoma | 52 | 45 | | 7 |
| 6 | Cancer of Stomach | 28 | 26 | | 2 |
| 7 | Cancer of Colon | 31 | 27 | | 4 |
| 8 | Cancer of Pancreas | 10 | 8 | | 2 |
| 9 | Miscellaneous | 29 | 25 | | 4 |
| | Total Patients | 424 | 382 | 7 | 35 |

Example 2

The following describes testing of fresh urine samples. 2 ml of urine is dropped in a quartz cuvette. The excitation wavelength was set at 325 nm, and the fluorescence emission spectrum was obtained from 350 to 600 nm. There was a smooth fluorescence band with a peak around 420 to 450 nm with a high intensity for healthy urine. There was a weak shoulder around 550 nm. The intensity ratio may be given as follows:

$R_6 = I_{500}/I_{450} < 0.3$

Figure 4:
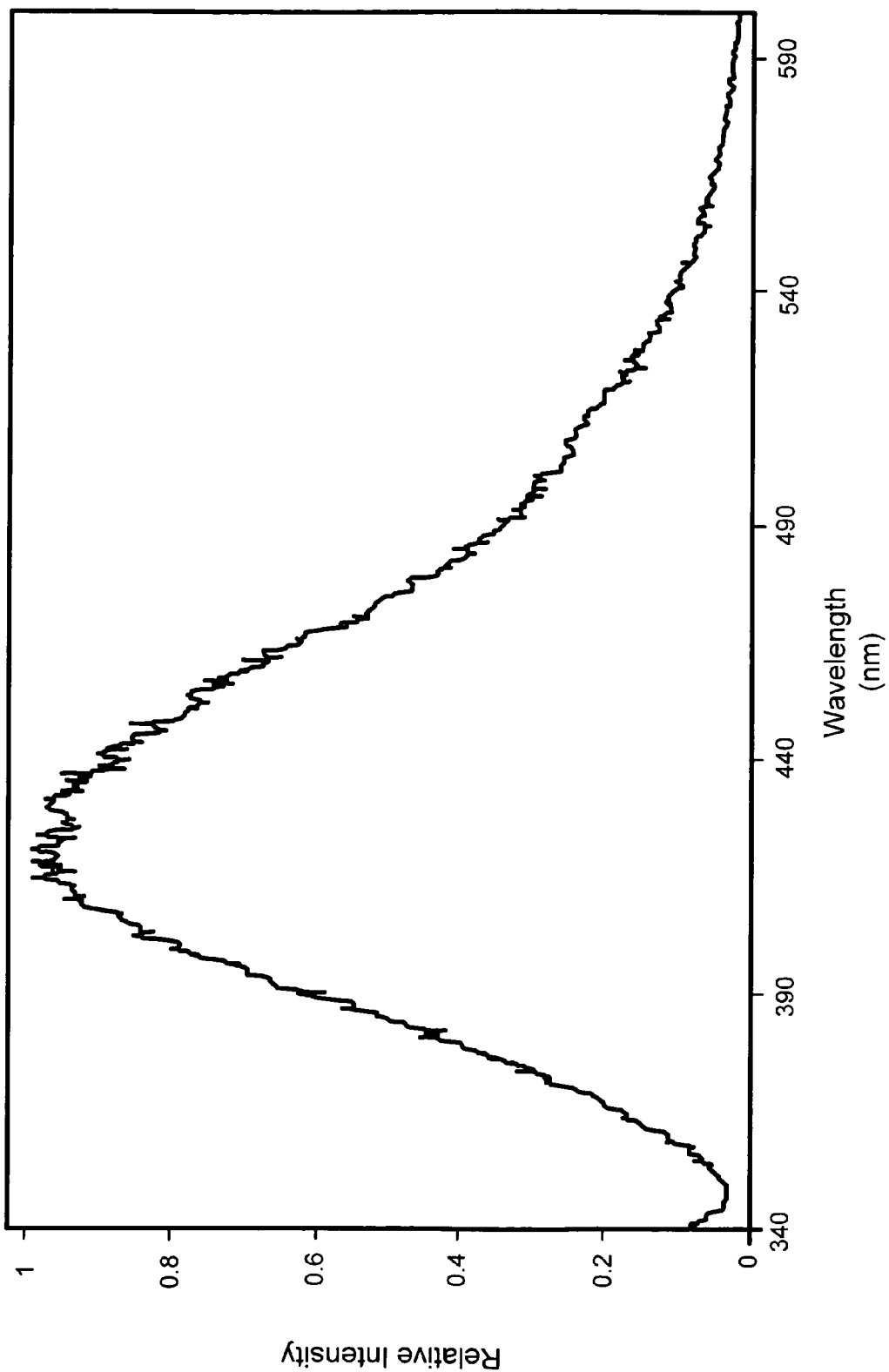
FIG. 4 shows the fluorescence emission spectrum of a urine sample from a healthy human patient at an excitation wavelength of 325 nm.

For a cancer-diseased patient, there are two bands, one around 500 nm and another around 550 nm, with an intensity ratio $R_6 = I_{500}/I_{450}$ varying from 0.4 to 2.0. Exemplary emission spectra for fresh urine samples are shown in FIGS. 4 and 5.

But these bands are at least 10 times weaker than the fluorescence of healthy urine.

The fluorescence band around 550 nm is most probably due to a combination of flavins, biliverdin and bilirubin. This is at least two times higher in concentration in cancer patients as compared to the healthy subjects.

Figure 7:
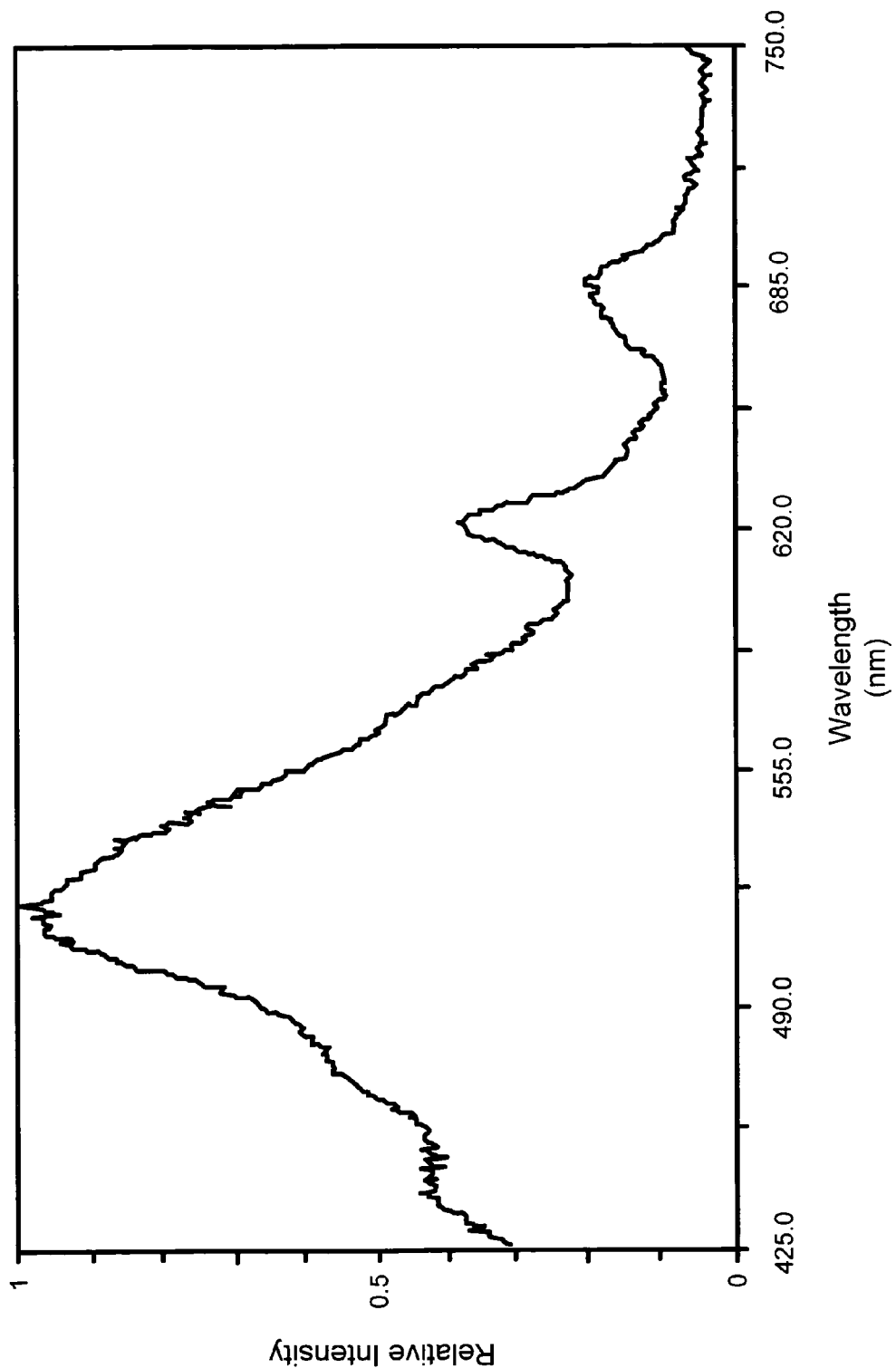
FIG. 7 shows the fluorescence emission spectrum of a urine sample at an excitation wavelength of 400 nm from a human patient afflicted with cancer.

Next, the excitation wavelength was fixed at 400 nm and fluorescence emission spectra were obtained from 425 nm to 700 nm. Exemplary spectra for this excitation wavelength are shown in FIGS. 6 and 7. There are many bands, including: 450 nm, 470 nm, 500 nm, 550 nm, 580 nm, 620 nm, and 685 nm. All but the 470 nm, 550 nm, and 620 nm bands, which are consistent, were ignored. The notation for the relevant ratios is:

$$R_7 = I_{620}/I_{470} \text{ and}$$

$$R_8 = I_{550}/I_{470}$$

If $R_7 < 0.5$ and $R_8 < 0.7$, the subject is healthy. But if $R_7 > 0.5$ and $R_8 > 0.7$, this implies that the subject has cancer.

Example 3

Extracts of urine were tested as follows. A reagent of ethyl acetate and acetic acid was prepared in the ratio of 4:1 (40 ml ethyl acetate to 10 ml acetic acid). In a test tube, 2 ml of reagent and 1 ml of urine were mixed. After shaking well, the mixture was allowed to settle for 10 minutes. The upper layer (about 1 ml), which had extracted cancer specific bio-molecules, was removed and subjected to fluorescence spectrography.

Figure 8:
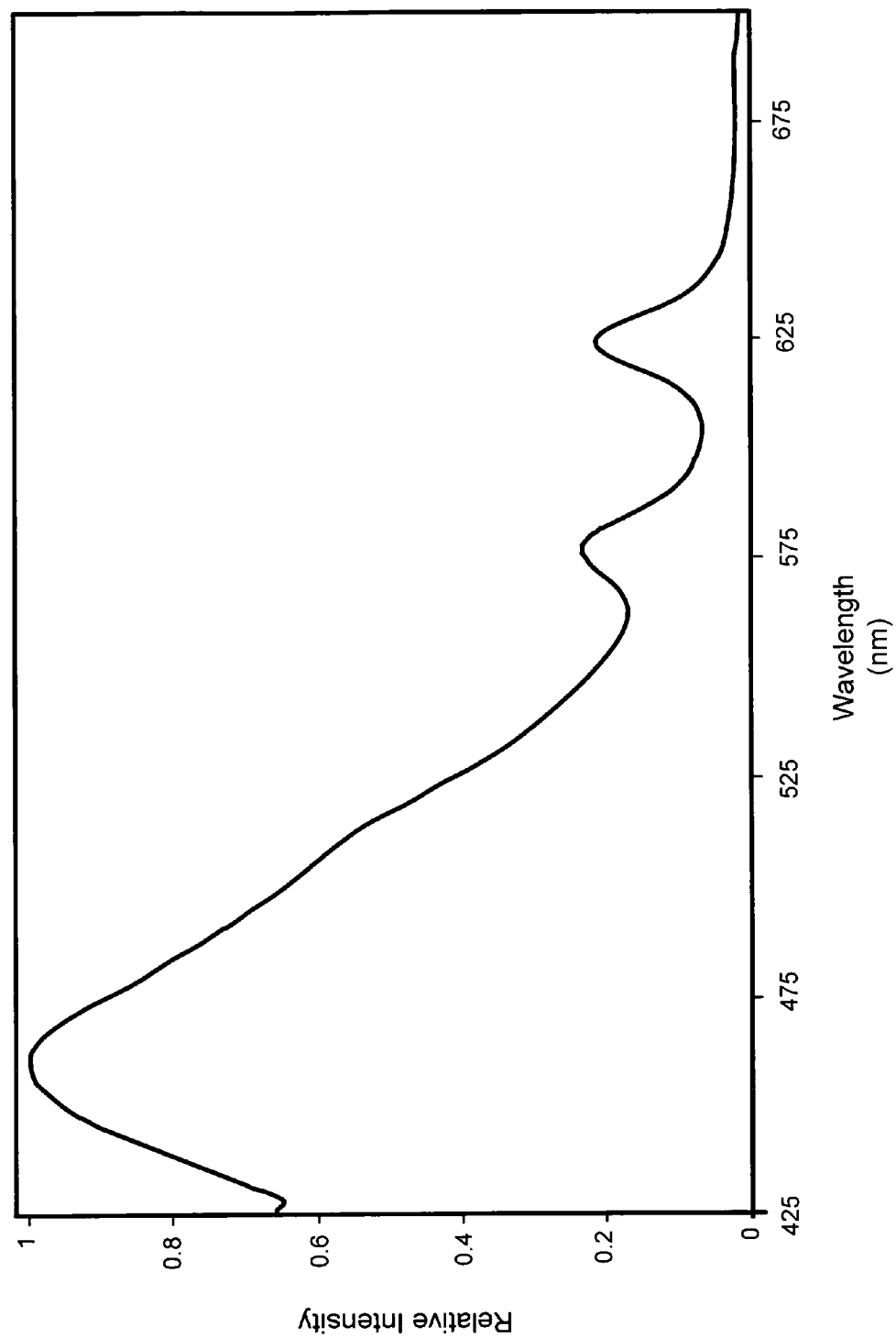
FIG. 8 shows the fluorescence emission spectrum of an extract of urine from a healthy human patient at an excitation wavelength of 400 nm.
Figure 9:
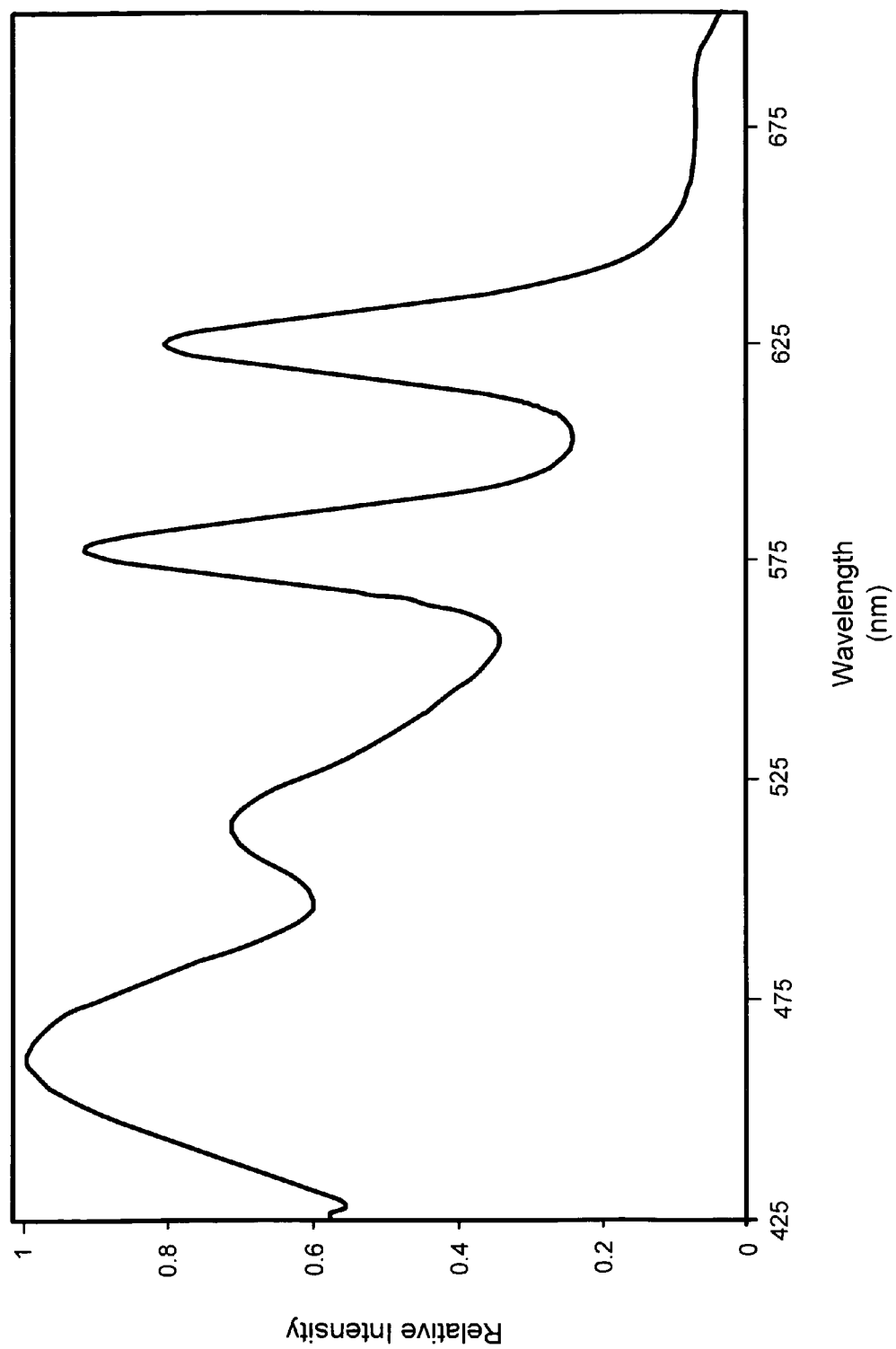
FIG. 9 shows the fluorescence emission spectrum of an extract of urine at an excitation wavelength of 400 nm from a human patient afflicted with cancer.

The wavelength was set at 400 nm, and the emission spectra from 425 nm to 720 nm were obtained. Exemplary spectra are shown in FIGS. 8 and 9. Four bands were obtained, including: (1) 460 nm due to Raman scattering of the reagents; (2) 525 nm due to flavins and bile components (biliverdin and bilirubin); (3) 575 nm due to porphyrins; and (4) 620 nm, also due to porphyrins. The intensity of all bands is measured. The notation may be given as follows:

$$R_9 = I_{620}/I_{525}$$

If $R_9 < 0.75$, the subject is healthy. If $0.75 < R_9 < 1.5$, the ratio implies the subject is in the early stages of cancer. If $R_9 > 1.5$, the ratio implies that the subject has an advanced stage of cancer.

Thus, nine parameters or intensity ratios are obtained for mass screening and detection of cancer from body fluids (blood and urine). The porphyrins, flavins, and also the bile components, which are found in higher concentrations in the body fluids of cancer patients than in the blood or urine of healthy patients, are the tumor markers. These bio-molecules (porphyrin, flavins, bilirubin, and biliverdin), are involved in heme metabolism. The concentrations of these bio-molecules appear to be considerably altered by substances released by cancer. These bio-molecules are the cancer specific fingerprints in laser- or light-induced fluorescence.

With the two above-mentioned body fluids and the above-mentioned parameters (intensity ratios), cancer detection can be done with a reliability factor of 80%.

Example 4

The optical analysis of body fluids can be extended to encompass excitation spectra, the emission wavelength being fixed, in order to improve the specificity and reliability of the method.

Figure 10:
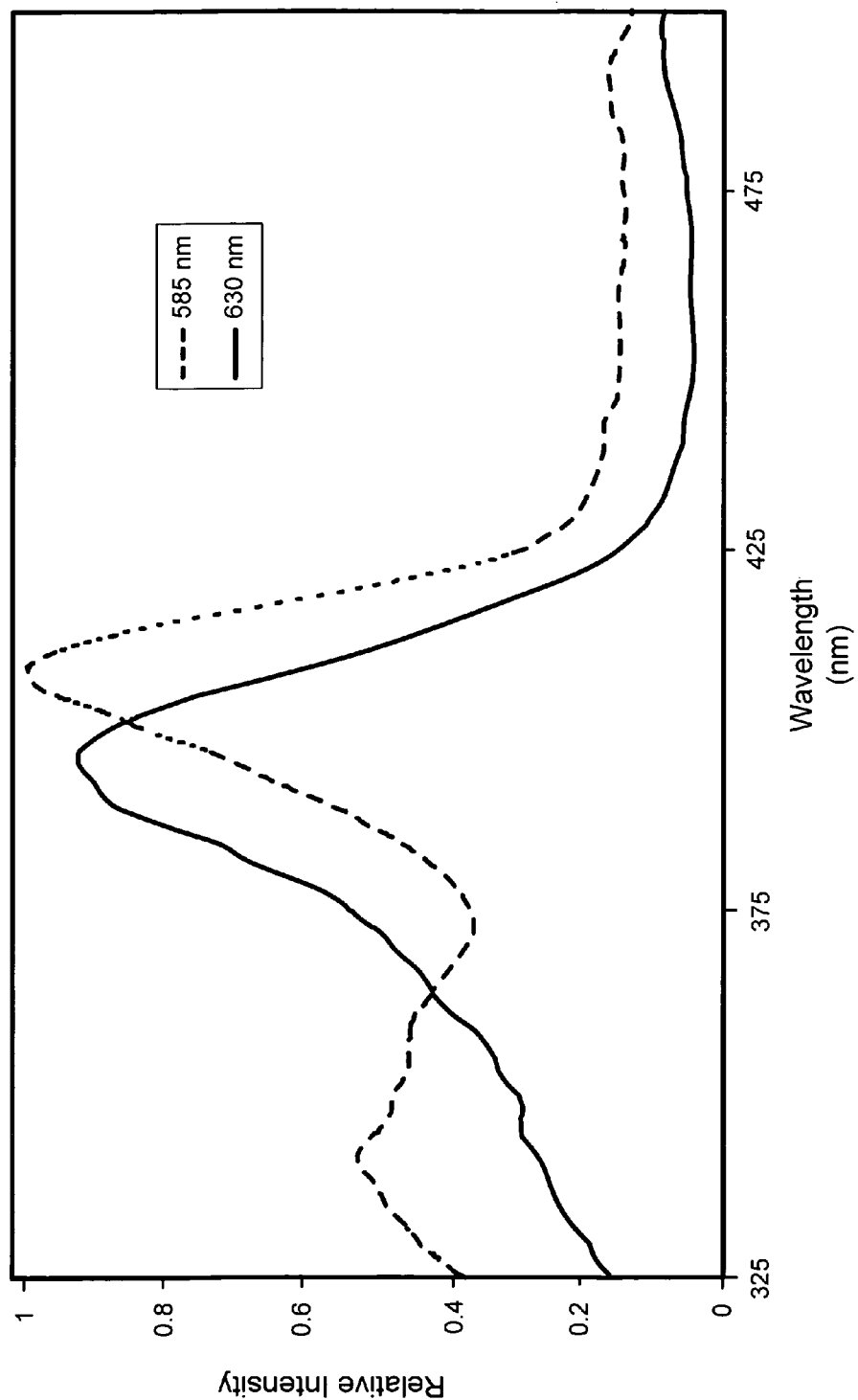
FIG. 10 shows the fluorescence excitation spectrum of a sample extract of the formed elements (mostly blood cells) from the blood of a healthy human patient, with the emission fixed at 585 nm (dashed line) and 630 nm (solid line).
Figure 11:
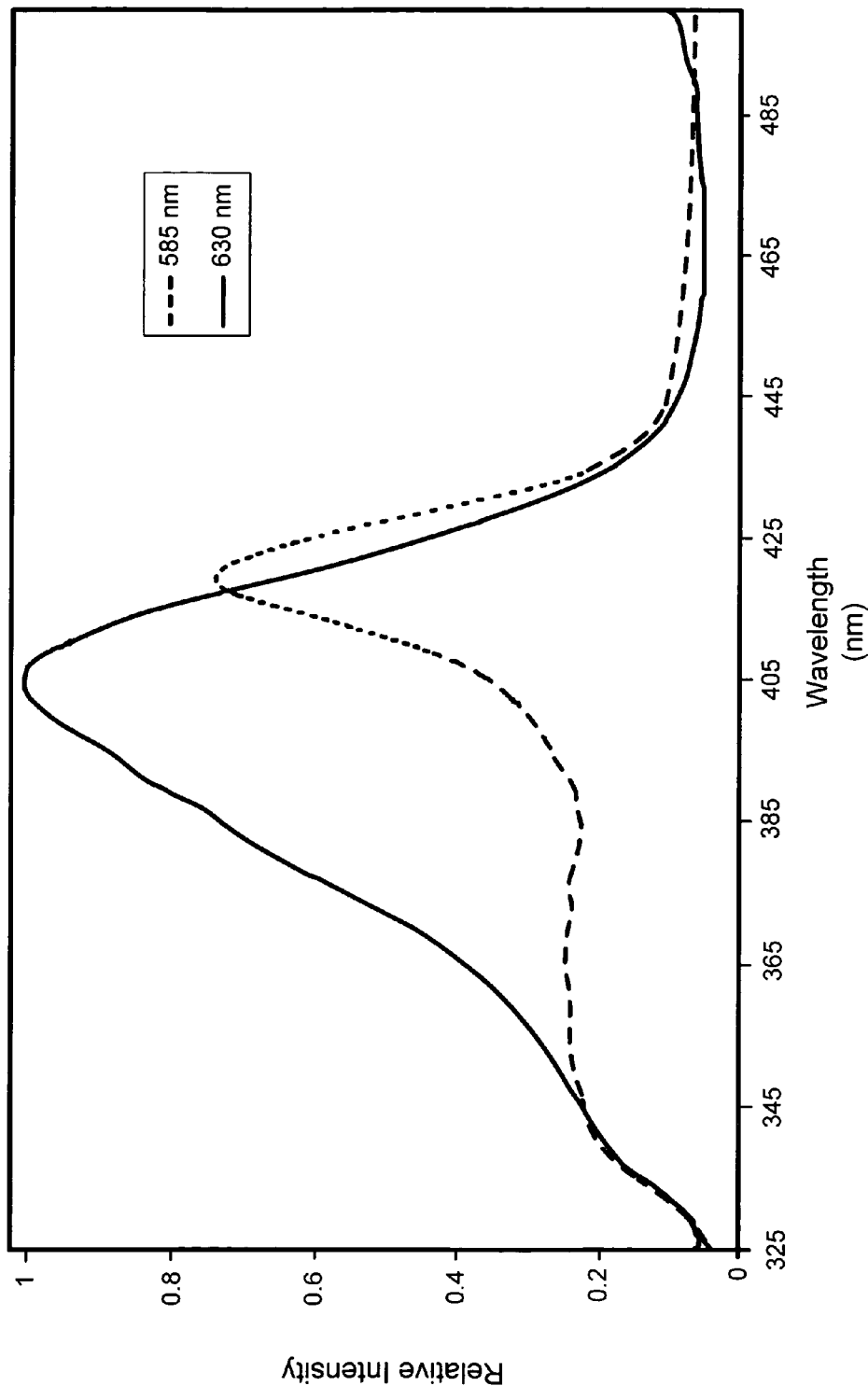
FIG. 11 shows the fluorescence excitation spectrum of a sample extract of the formed elements (mostly blood cells) from the blood of a human patient afflicted with cancer, with the emission fixed at 585 nm (dashed line) and 630 nm (solid line).

The sample, whether of the extract of blood, a sample of urine, etc., is prepared as described above and placed in the quartz cuvette. The emission wavelength is fixed at 630 nm, and the excitation spectrum is scanned from 350 to 600 nm. The excitation spectrum exhibits a primary peak around 398 nm, and a few secondary peaks. The intensity of $I_{398}$ is measured. Then the emission wavelength is fixed at 585 nm, and the excitation a spectrum is scanned from 300 nm to 550 nm. This gives another excitation spectrum that is very similar to the previous spectrum, but with a peak at 410 nm. These two spectra are the excitation spectra of two species of porphyrin. FIGS. 10 and 11 show exemplary excitation spectra for healthy and cancerous subjects, respectively.

The peak intensity of the two bands is measured. The ratio of the intensities is denoted as follows:

$$R_{10} = I_{398}/I_{410}.$$

The significance of the ratio is that if $R_{10} < 0.8$, the subject is healthy. If $0.8 < R_{10} < 1.5$, the ratio implies that the subject is in the early stages of cancer. If $R_{10} > 1.5$, the ratio implies that the subject is in the advanced stages of cancer.

Example 5

The optical analysis of body fluids can be extended to encompass synchronous excitation spectra, the emission wavelength being fixed, in order to improve the specificity and reliability of the method. This becomes an additional window of analysis. This is a compounded spectrum of fluorescence emission of many molecules, but with each molecule being excited at the absorption peak. It gives a better resolution and identification of a weakly fluorescing, submerged fluorophore.

A sample of blood plasma was prepared and placed in a transparent quartz cuvette. The excitation wavelength was set at 200 nm and the emission wavelength was set at 210 nm, with an offset wavelength difference of 10 nm. Then, both the excitation spectrum and the emission spectrum are scanned simultaneously at the same rate in order to maintain the 10 nm offset between the spectra. This produces a narrower bandwidth and higher resolution. The spectra were scanned up to 700 nm.

Such synchronous spectra obtained for any sample show distinct and marked differences between samples from healthy subjects and samples from subjects afflicted with cancer.

Figure 12:
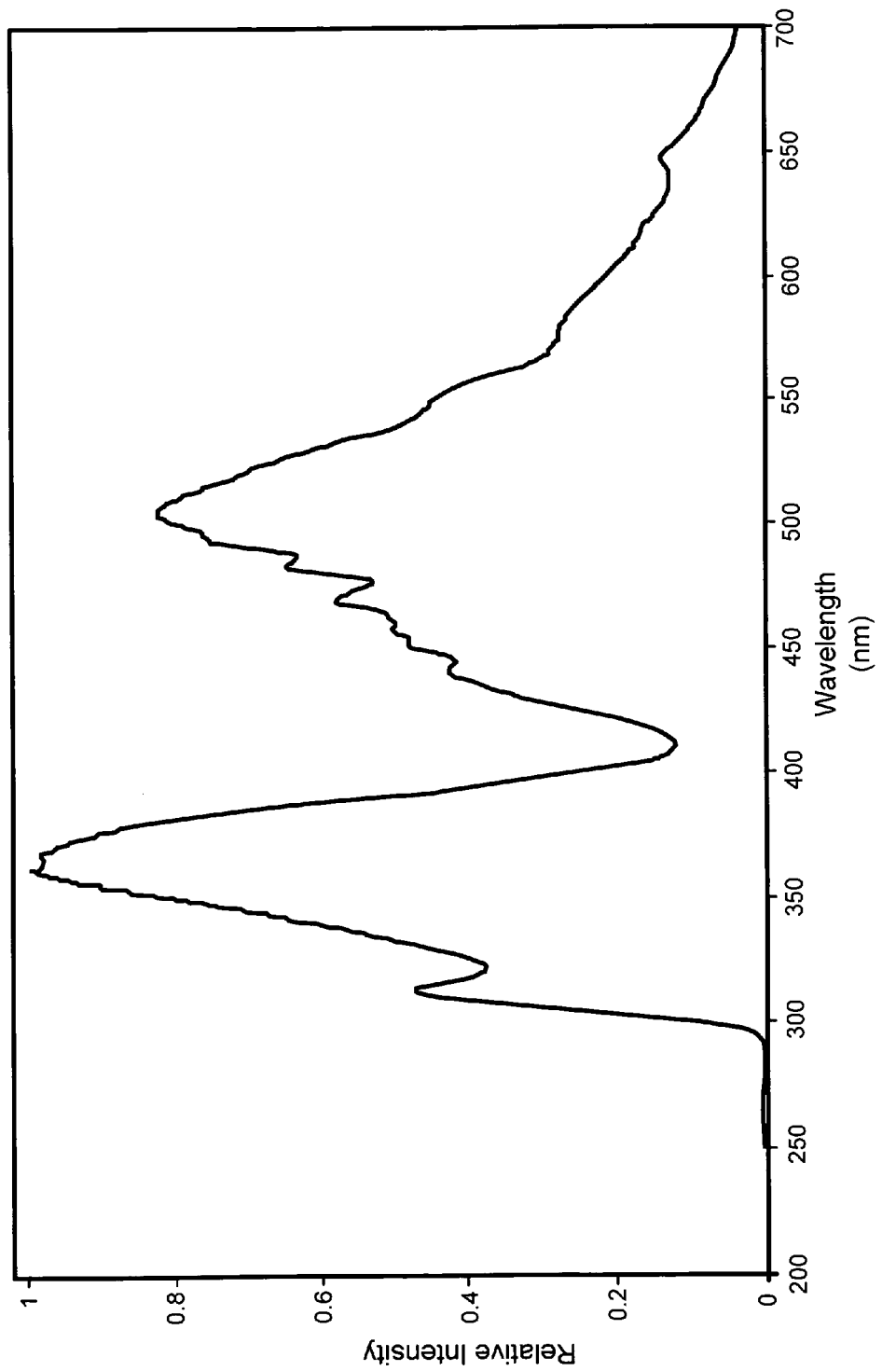
FIG. 12 shows the synchronous fluorescence spectrum of a sample of blood plasma of a healthy human patient, with an offset of 10 nm between the excitation and emission wavelengths.
Figure 13:
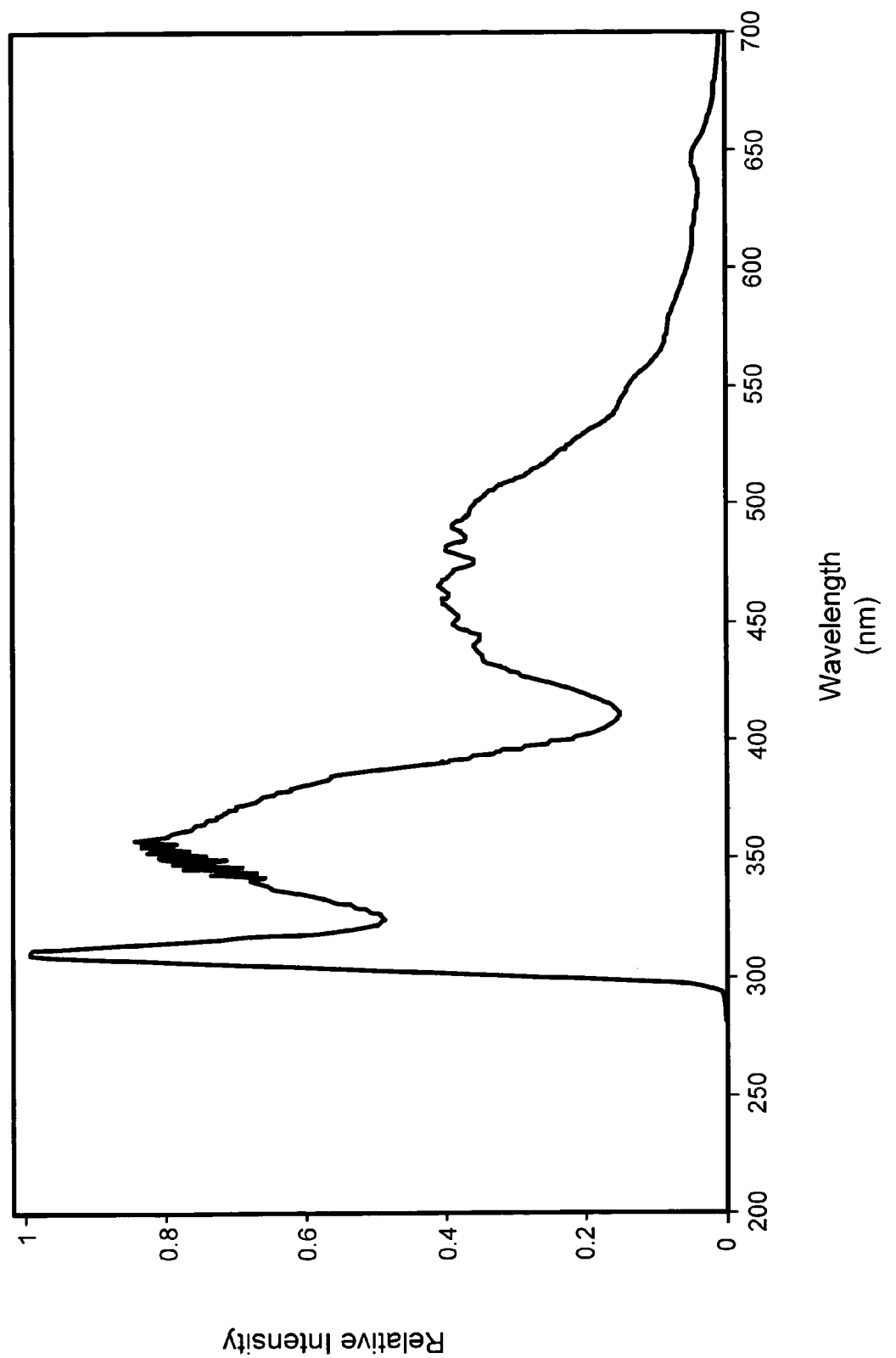
FIG. 13 shows the synchronous fluorescence spectrum of a sample of blood plasma of a human patient afflicted with cancer, with an offset of 10 nm between the excitation and emission wavelengths.

There are well-defined bands around 311 nm, 365 nm, 450 nm, 505 nm, 550 nm, and 620 nm. Since plasma contains a host of free and enzyme bound fluorophores (bio-molecules), bands can only be tentatively assigned to the fluorophores. Of these, 311 nm is the sharp band of the amino acid, tyrosine. The 365 nm band is most likely due to tryptophan (sometimes also written "tryptophane"). The 450 band is due to NAD(P)H; the 505 nm band is due to riboflavin; the 550 nm band is due to bilirubin; and the 585 nm and 625 nm bands are due to porphyrins. Comparing the healthy subject's spectra to the cancerous subject's spectra, it is apparent that these bio-molecules are out of proportion in the cancerous subject's blood sample. Exemplary synchronous spectra for the healthy subject and cancerous subject are shown in FIGS. 12 and 13, respectively.

For example, the ratio of the band at 311 nm (due to tyrosine) and at 365 nm (due to tryptophan) is 0.7 for healthy and 1.8 for advanced stages of cancer (so the contrast parameter is 2.6). This ratio is 1.05 for early cancer and 0.83 for high risk or hyperplasia.

Another important ratio is the ratio of concentrations or intensities between tryptophan and porphyrin. This ratio ($I_{365}/I_{585}$) is 2.3 for healthy, 3/5 for high-risk cases, 4.5 for early cancer, and 8.7 for advanced cases of cancer. Other similar fluorescence ratios are given in Table III, below.

TABLE III

| | Synchronous Spectra of Blood Plasma | | | | |
|---|---|---|---|---|---|
| Ratio | Healthy | High Risk | Early Cancer | Advanced Cancer | Contrast Parameter |
| $R_{11} = I_{311}/I_{365}$ | 0.7 | 0.83 | 1.05 | 1.8 | 2.6 |
| $R_{12} = I_{365}/I_{505}$ | 1 | 1.3 | 1.6 | 2.35 | 2.35 |
| $R_{13} = I_{365}/I_{550}$ | 1.7 | 2.5 | 3.4 | 5.5 | 3.2 |
| $R_{14} = I_{365}/I_{585}$ | 2.3 | 3.5 | 4.5 | 8.7 | 4 |
| $R_{15} = I_{450}/I_{500}$ | 0.45 | 0.7 | 0.9 | 1.1 | 2.4 |
| $R_{16} = I_{450}/I_{550}$ | 0.9 | 1.4 | 1.8 | 2.2 | 2.6 |

Figure 14:
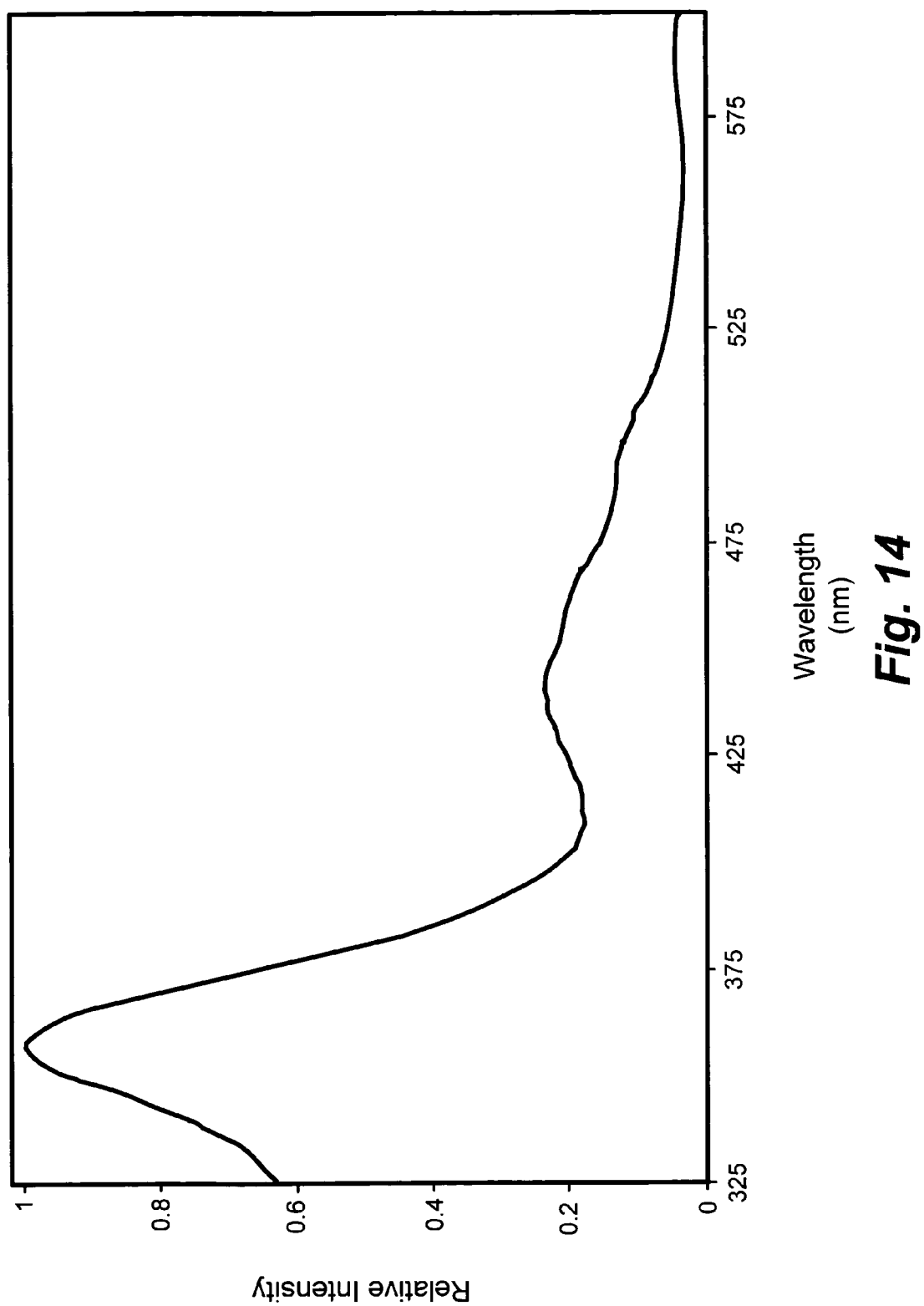
FIG. 14 shows the synchronous fluorescence spectrum of a sample of blood plasma of a healthy human patient, with an offset of 70 nm between the excitation and emission wavelengths.
Figure 15:
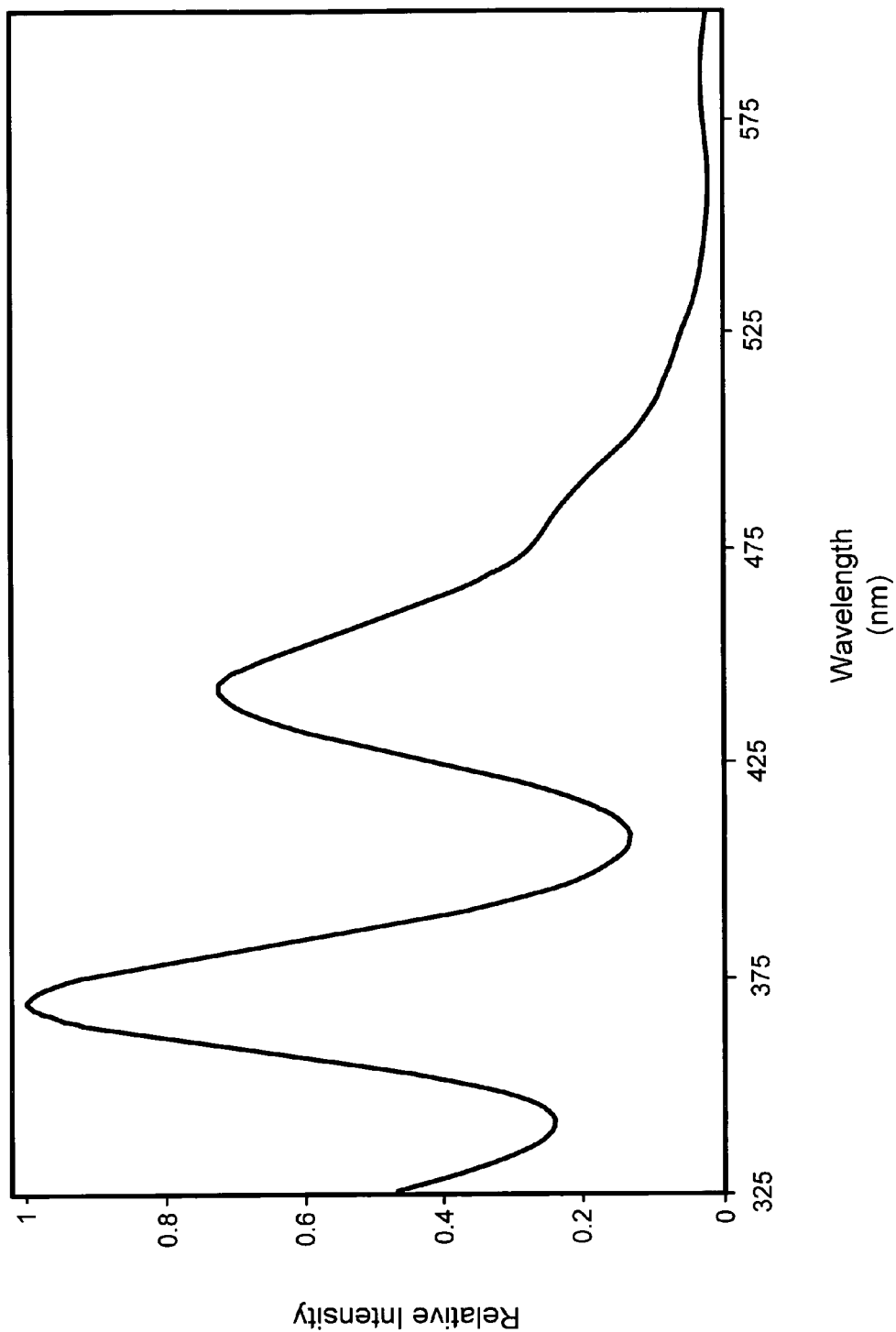
FIG. 15 shows the synchronous fluorescence spectrum of a sample of blood plasma of a human patient afflicted with cancer, with an offset of 70 nm between the excitation and emission wavelengths.

Next, synchronous spectra are obtained with the offset between the excitation and emission wavelengths set at 70 nm. Exemplary spectra for the healthy subject and the cancerous subject are shown in FIGS. 14 and 15, respectively. In this case, there are two bands of fluorescence, one at 355 nm and another at 450 nm, plus a third band at 500 nm. An intensity ratio is defined for:

$$R_{17} = I_{450}/I_{355}$$

This ratio is about 0.4 for healthy, 0.6 for early cancer, and greater than 1 for advanced cancer. In this ratio, 355 nm is the excitation wavelength for NAD(P)H and 450 nm is for flavins and bilirubin.

Figure 16:
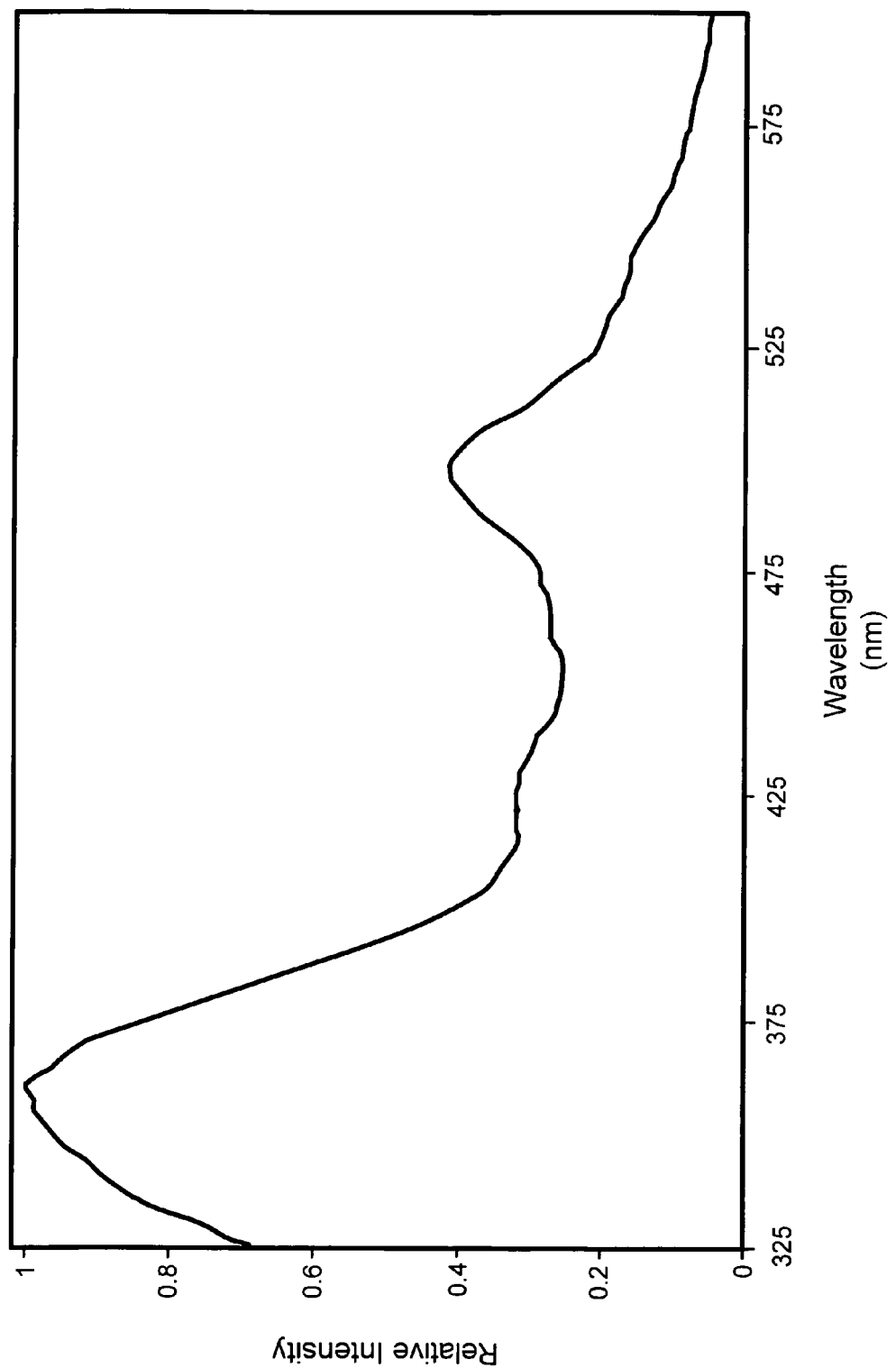
FIG. 16 shows the synchronous fluorescence spectrum of a sample of blood plasma of a healthy human patient, with an offset of 30 nm between the excitation and emission wavelengths.
Figure 17:
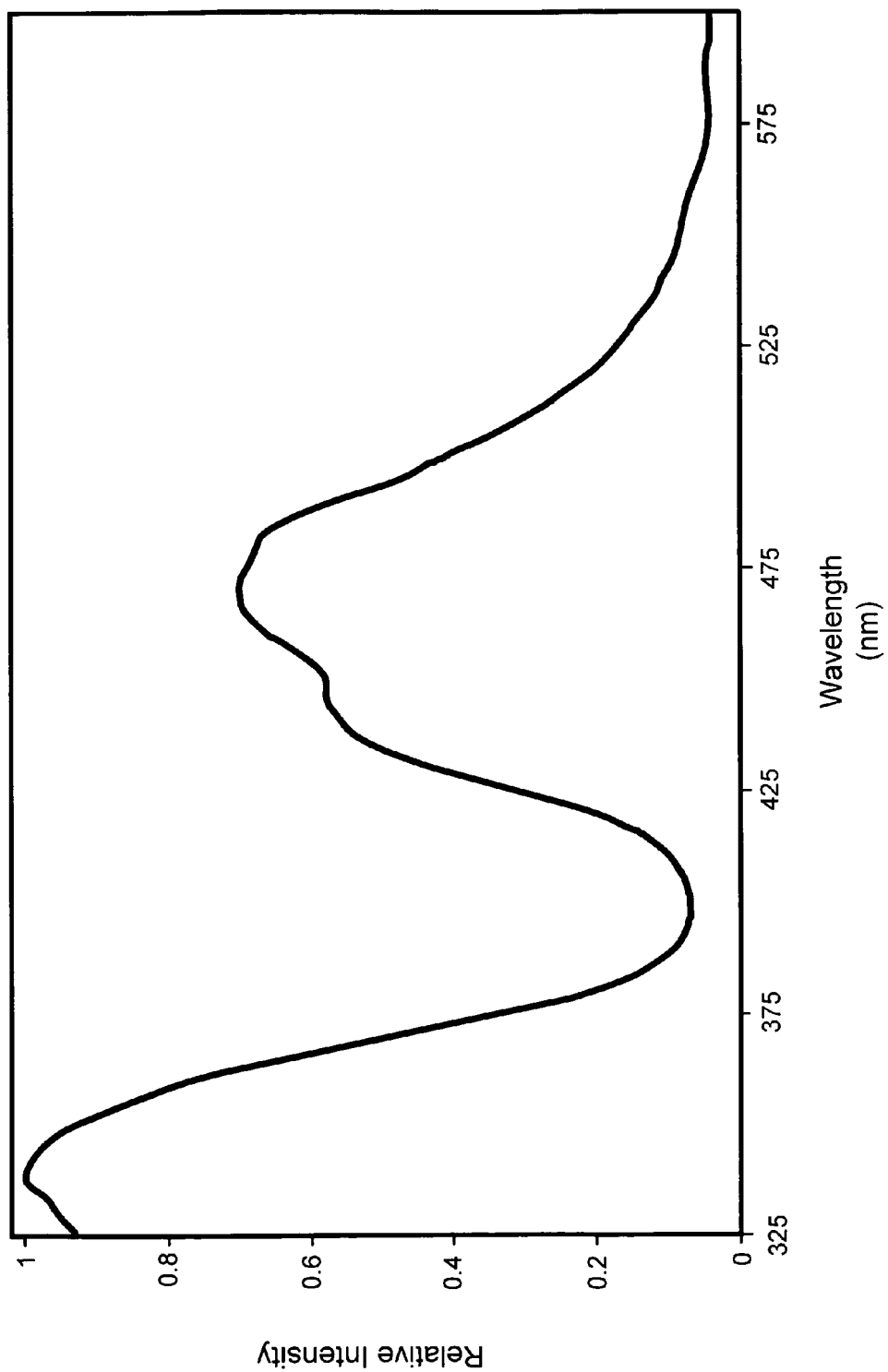
FIG. 17 shows the synchronous fluorescence spectrum of a sample of blood plasma of a human patient afflicted with cancer, with an offset of 30 nm between the excitation and emission wavelengths.

Finally, the offset between the excitation and emission wavelengths is set for 30 nm and synchronous spectra are obtained. Exemplary spectra for the healthy subject's sample and the cancerous subject's sample are shown in FIGS. 16 and 17, respectively. Two bands are obtained, one at 355 nm and the other at 480 nm. The ratio of intensities is defined as:

$$R_{18} = I_{480}/I_{355}$$

A ratio of $R_{18} < 0.4$ implies the subject is healthy. A ratio of $R_{18} > 0.4$ implies the subject has cancer. Again, the peak absorption wavelengths indicate elevation of flavins and bilirubin.

Example 6

Figure 18:
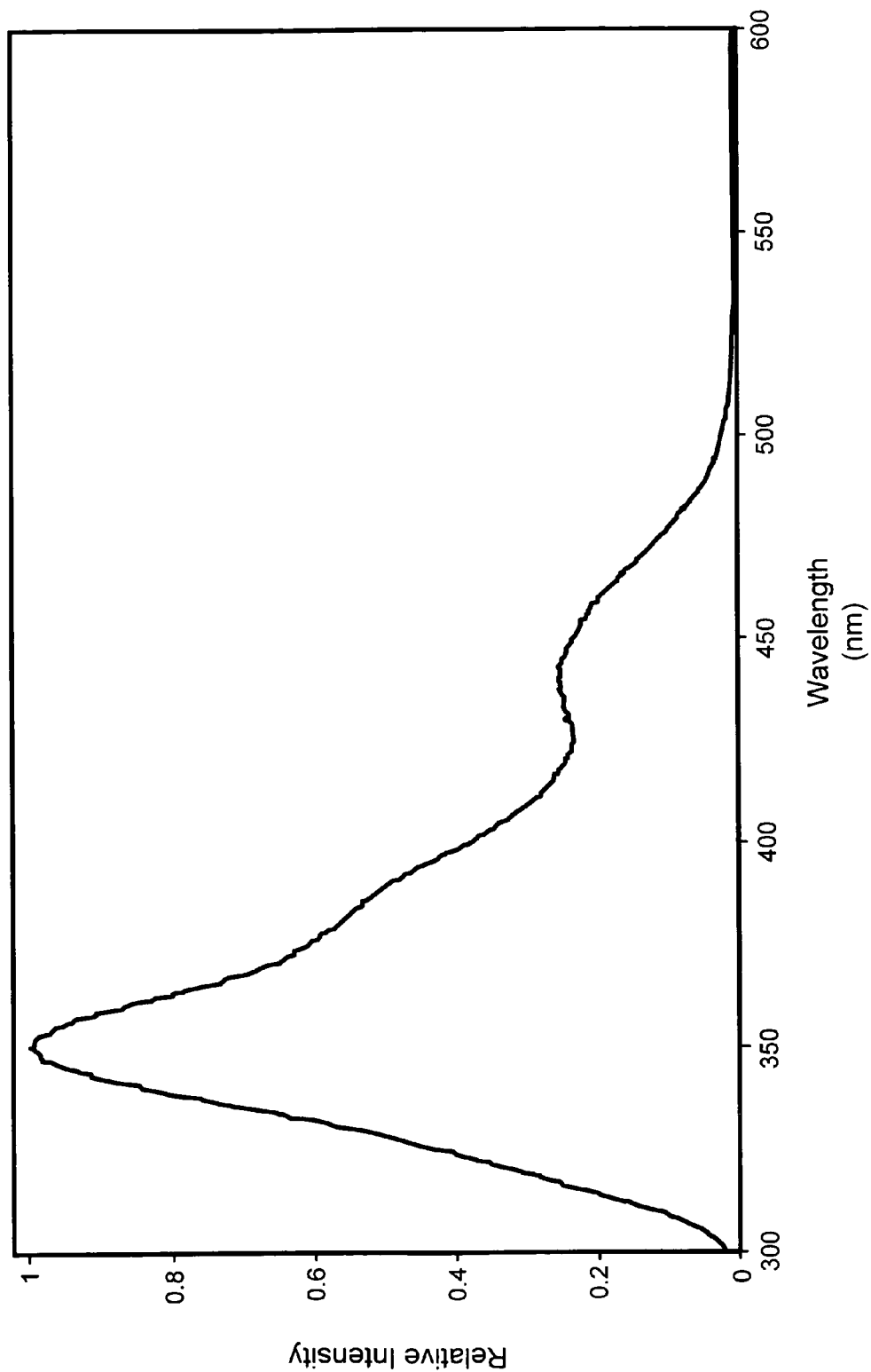
FIG. 18 shows the synchronous fluorescence spectrum of a urine sample of a healthy human patient, with an offset of 70 nm between the excitation and emission wavelengths.
Figure 19:
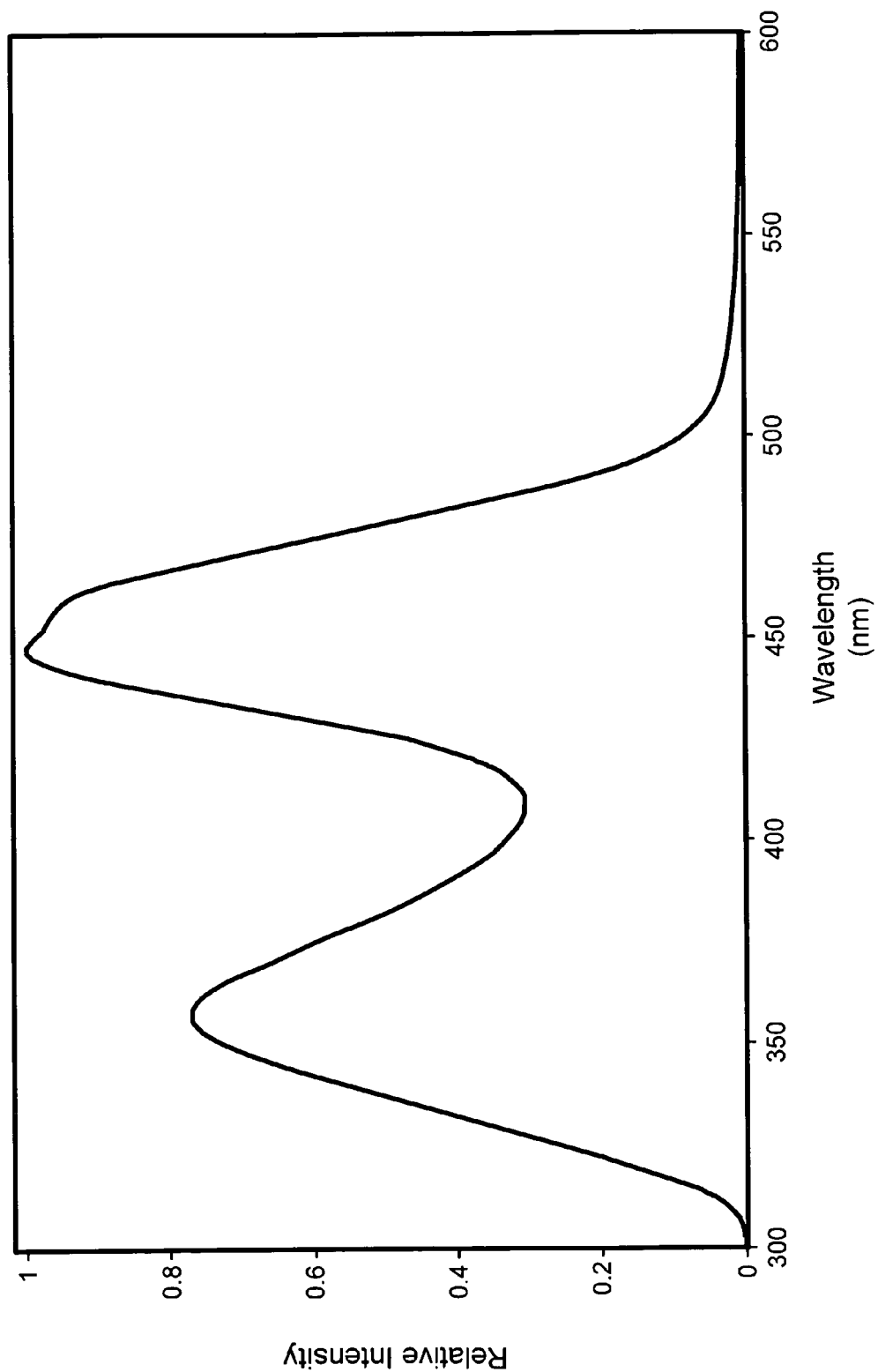
FIG. 19 shows the synchronous fluorescence spectrum of a urine sample of a human patient afflicted with cancer, with an offset of 70 nm between the excitation and emission wavelengths.

Synchronous spectra can also be used to analyze urine samples. A 2 ml sample of fresh urine is placed in the cuvette. Synchronous spectra are run from 325 nm to 700 nm with an offset of 70 nm between the excitation and emission wavelengths. Exemplary spectra for a healthy subject's sample and a cancerous subject's sample are shown in FIGS. 18 and 19, respectively. The intensities at 355 nm and 450 nm (corresponding to NAD(P)H and bilirubin) are picked out. The ratio of intensities is defined as:

$$R_{19} = I_{450}/I_{355}$$

A ratio of $R_{19} < 1$ implies the subject is healthy. When $1 < R_{19} < 2$, the ratio implies the subject is in the early stages of cancer. A ratio of $R_{19} > 2$ implies the subject is in the advanced stages of cancer.

Figure 20:
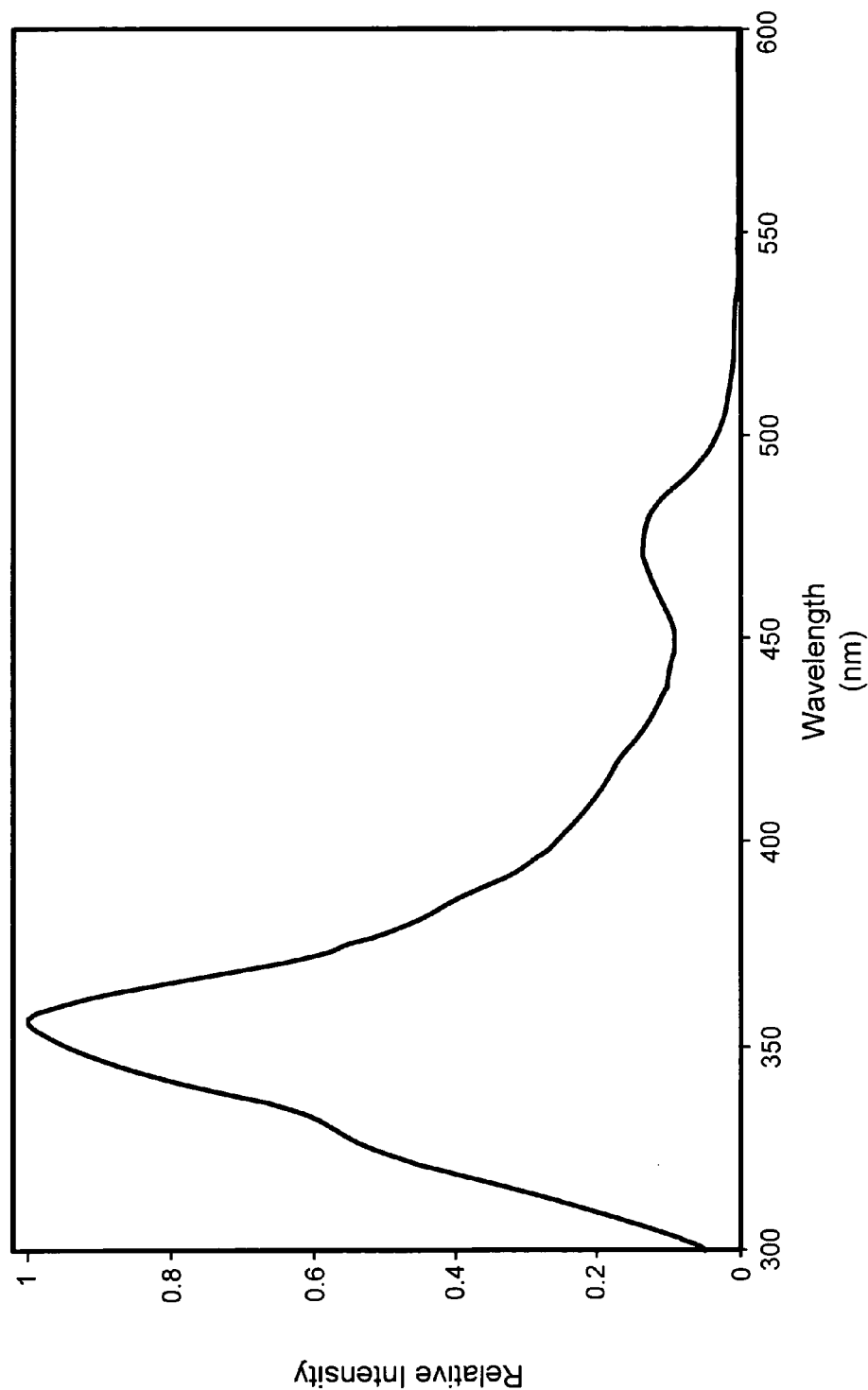
FIG. 20 shows the synchronous fluorescence spectrum of a urine sample of a healthy human patient, with an offset of 30 nm between the excitation and emission wavelengths.
Figure 21:
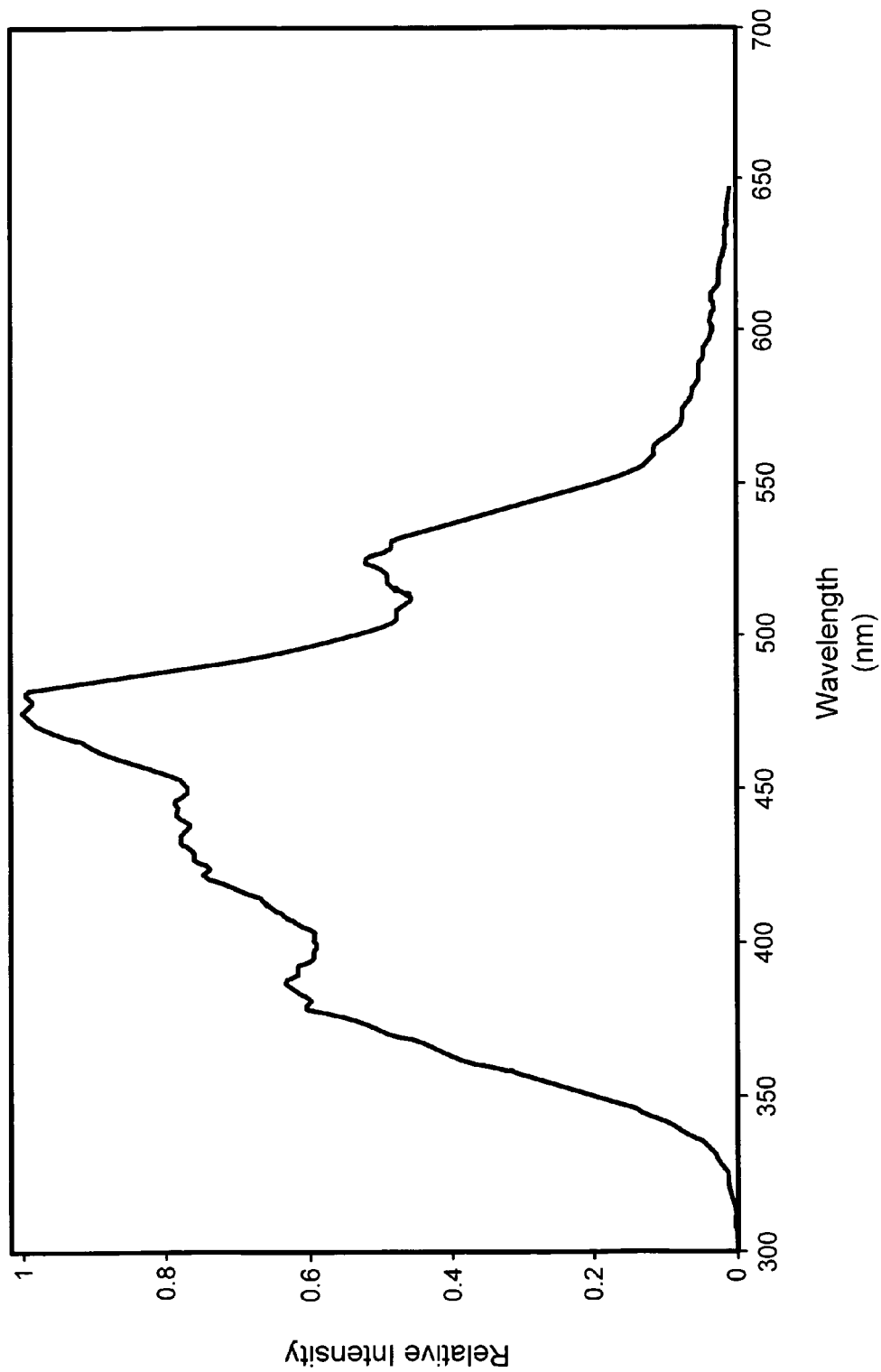
FIG. 21 shows the synchronous fluorescence spectrum of a urine sample of a human patient afflicted with cancer, with an offset of 30 nm between the excitation and emission wavelengths.

Synchronous spectra are run on the same sample from 300 nm to 700 nm, this time with an offset of 30 nm between the excitation and emission wavelengths. Exemplary spectra for a healthy subject's sample and a cancerous subject's sample are shown in FIGS. 20 and 21, respectively. The intensities at 355 nm and 480 nm (corresponding to NAD(P)H and bilirubin) are picked out. The ratio of intensities is defined as:

$$R_{20} = I_{480}/I_{355}$$

A ratio of $R_{20} < 1.5$ implies the subject is healthy. When $1.5 < R_{20} < 4$, the ratio implies the subject is in the early stages of cancer. A ratio of $R_{20} > 4$ implies the subject is in the advanced stages of cancer.

The inventors have done a study to diagnose cancer from urine alone (without any analysis of blood). Out of 178 samples of urine, 50 were from healthy volunteers of age 30-55 and 128 from diseased patients (mostly cancer of the cervix or breast). The optical diagnosis using fluorescence spectroscopy is more than 80% reliable, as shown in Table IV below.

TABLE IV

| | Urine Analysis | | | |
|---|---|---|---|---|
| Subjects | Number | Correct Optical Diagnosis | False Positive | False Negative |
| Healthy | 50 | 45 | 5 | |
| Pre-malignant | 15 | 12 | | 3 |
| Cancer | 113 | 102 | | 11 |
| Total | 178 | 159 | 5 | 14 |

Example 7

In order to confirm that the optical analysis of body fluids can be carried out with either lamp excitation or a coherent light source, the fluorescence emission tests were repeated using a Titanium-Sapphire laser as the excitation light source. The Ti-sapphire is readily available in the market and is used as such. The laser was pumped by a pulsed Nd YAG laser at 532 nm, and the frequency doubled Ti-sapphire laser was tunable from 350 nm to 420 nm. The laser was tuned to 400 nm, and the laser pulse of 5 millijoules of energy and 10 ns pulse width was directed at the sample in the cuvette. The laser-induced fluorescence was collected at right angles to the incident laser and analyzed using a grating and a diode array. The test was done with the following samples: (1) Plasma, Extract of Formed Elements; and (2) Urine and Extracts of Urine.

Figure 22:
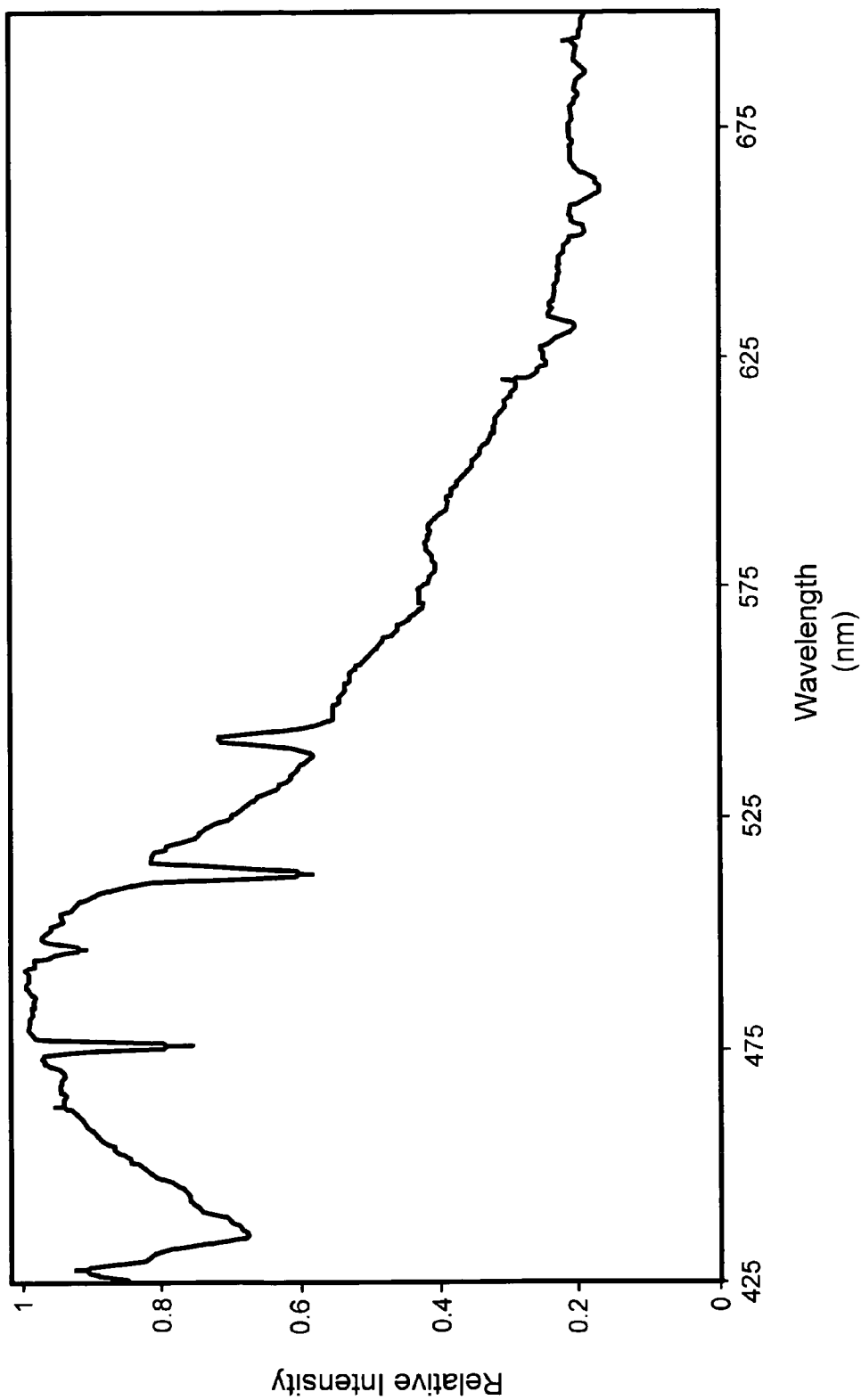
FIG. 22 shows the fluorescence emission spectrum of a urine sample from a healthy human patient at an excitation wavelength of 400 nm using a pulsed Ti-sapphire laser.
Figure 23:
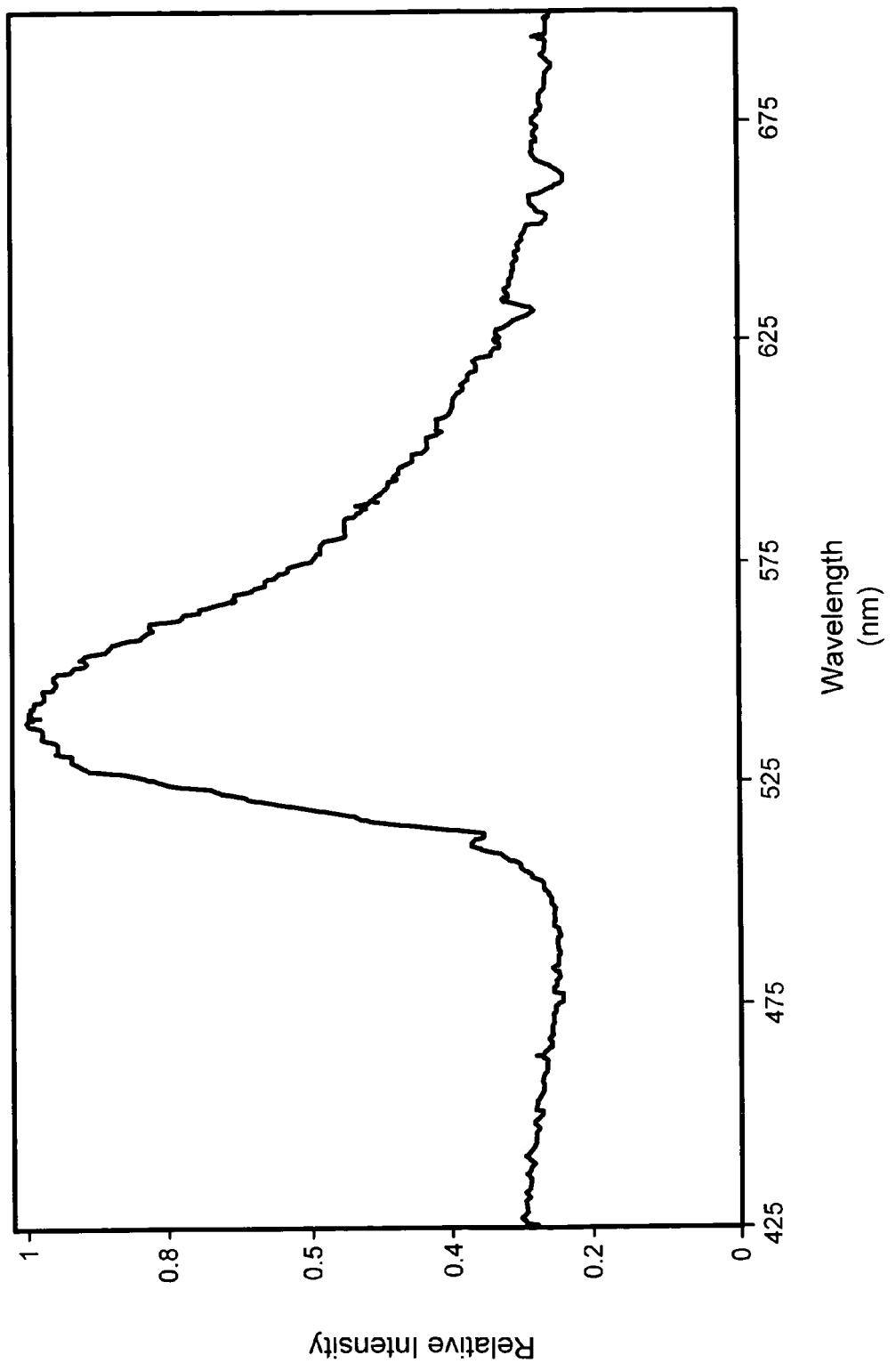
FIG. 23 shows the fluorescence emission spectrum of a urine sample at an excitation wavelength of 400 nm from a human patient afflicted with cancer using a pulsed Ti-sapphire laser.

Exemplary FIGS. 22 and 23 show the Laser Induced Fluorescence (LIF) of urine of a healthy subject and of a cancer diseased patient, respectively.

The intensity ration $I_{550}/I_{470}$ is about 0.4 for the healthy subject and about 1 for the cancerous subject, which is comparable to the results of the lamp excitation test. In a similar manner, all other samples show the same trend. LIF spectra need more expensive instrumentation, but without any additional advantage in the quality of the data.

It is to be understood that the present invention is not limited to the embodiments described above, but encompasses any and all embodiments within the scope of the following claims.

We claim:

1. A method for optical analysis of body fluids, comprising the steps of:
   irradiating a sample of a body fluid with light from an optical source at a wavelength of about 400 nm;
   detecting fluorescence from the sample over an emission band extending from about 425 nm to 700 nm;
   identifying and measuring fluorescence intensity maxima in the emission band corresponding to species of porphyrin, flavins, bile components, and background sample media; and comparing relative concentrations of the species of porphyrin, flavins, bile components, and background sample media from the fluorescence intensities in order to diagnose cancer condition in a subject from whom the sample is taken.

2. The method for optical analysis of body fluids according to claim 1, wherein said step of irradiating the body fluid comprises irradiating an extract of formed elements from blood, the method further comprising the steps of:
 withdrawing a sample of blood from the subject;
 separating plasma from the formed elements of blood in the sample of blood;
 decanting the plasma to leave a residue of blood components; and
 extracting the residue of blood components with an extraction solvent to form the extract of formed elements from blood.

3. The method for optical analysis of body fluids according to claim 2, wherein said step of identifying and measuring fluorescence intensity maxima further comprises:
 measuring the fluorescence intensity at about 460 nm, corresponding to Raman scattering from the extraction solvent;
 measuring the fluorescence intensity at about 505 nm, corresponding to flavins and bile components;
 measuring the fluorescence intensity at about 585 nm, corresponding to anionic species of porphyrin;
 measuring the fluorescence intensity at about 630 nm, corresponding to neutral species of porphyrin; and
 measuring the fluorescence intensity at about 695 nm, corresponding to cationic species of porphyrin.

4. The method for optical analysis of body fluids according to claim 3, wherein said step of comparing relative concentrations further comprises the step of computing a ratio of the fluorescence intensity of the neutral species of porphyrin to the fluorescence intensity of the anionic species of porphyrin.

5. The method for optical analysis of body fluids according to claim 4, further comprising the step of tentatively diagnosing the subject as:
 free of cancer when the ratio is less than 1.5;
 at high risk for cancer when the ratio is greater than 1.5 and less than 2.25;
 in the early stages of cancer when the ratio is greater than 2.25 and less than 3; and
 in the advanced stages of cancer when the ratio is greater than 3.

6. The method for optical analysis of body fluids according to claim 5, further comprising the step of planning a course of further diagnostic testing and treatment according to the tentative diagnosis.

7. The method for optical analysis of body fluids according to claim 3, wherein said step of comparing relative concentrations further comprises the step of computing a ratio of the fluorescence intensity of the cationic species of porphyrin to the fluorescence intensity of the anionic species of porphyrin.

8. The method for optical analysis of body fluids according to claim 3, wherein said step of comparing relative concentrations further comprises the step of computing a ratio of the fluorescence intensity of the neutral species of porphyrin to the fluorescence intensity of the flavins and bile components.

9. The method for optical analysis of body fluids according to claim 3, wherein said step of comparing relative concentrations further comprises the step of computing a ratio of the fluorescence intensity of the anionic species of porphyrin to the fluorescence intensity of the background sample media.

10. The method for optical analysis of body fluids according to claim 9, further comprising the step of tentatively diagnosing the subject as having Hodgkin's lymphoma when the ratio is between about 0.5 and 1.5.

11. The method for optical analysis of body fluids according to claim 3, wherein said step of comparing relative concentrations further comprises the step of computing a ratio of the fluorescence intensity of the flavins and bile components to the fluorescence intensity of the background sample media.

12. The method for optical analysis of body fluids according to claim 1, wherein said step of irradiating the body fluid comprises irradiating an a sample of fresh urine.

13. The method for optical analysis of body fluids according to claim 1, wherein said step of comparing relative concentrations further comprises the steps of:
 measuring the fluorescence intensity at about 470 nm, corresponding to Raman scattering from the background sample media;
 measuring the fluorescence intensity at about 550 nm, corresponding to bilirubin; and
 measuring the fluorescence intensity at about 620 nm, corresponding to porphyrin.

14. The method for optical analysis of body fluids according to claim 1, wherein said step of irradiating the body fluid comprises irradiating an a sample of an extract from urine, the urine being extracted with an extraction solvent.

15. The method for optical analysis of body fluids according to claim 1, wherein said step of comparing relative concentrations further comprises the steps of:
 measuring the fluorescence intensity at about 460 nm, corresponding to Raman scattering from the background sample media;
 measuring the fluorescence intensity at about 525 nm, corresponding to bile components;
 measuring the fluorescence intensity at about 575 nm, corresponding to a species of porphyrin
 measuring the fluorescence intensity at about 620 nm, corresponding to a species of porphyrin.

16. A method for optical analysis of body fluids, comprising the steps of:
 fixing a fluorescence detector to detect fluorescent emissions from a sample of a body fluid at a wavelength of about 630 nm;
 irradiating the sample with light from an optical source over an excitation band spectrum extending from about 350 nm to 600 nm;
 fixing the fluorescence detector to detect fluorescent emissions from the sample of the body fluid at a wavelength of about 585 nm;
 irradiating the sample with light from an optical source over an excitation band spectrum extending from about 300 nm to 550 nm;
 identifying and measuring absorption intensity maxima in the excitation spectra corresponding to species of porphyrin; and
 comparing relative concentrations of the species of porphyrin in order to diagnose cancer condition in a subject from whom the sample is taken.

17. The method for optical analysis of body fluids according to claim 16, wherein the body fluid is selected from the group consisting of blood plasma, an extract of formed elements derived from blood components, fresh urine, and an extract of components from urine.

18. The method for optical analysis of body fluids according to claim 16, wherein said step of identifying and measuring absorption intensity maxima further comprises measuring the absorption intensities at about 398 nm and 410 nm, said step of comparing further comprising computing a ratio of the absorption intensity at 398 nm to the absorption intensity at 410 nm.

19. A method for optical analysis of body fluids, comprising the steps of:
- irradiating a sample of a body fluid with light from an optical source over a band of excitation wavelengths extending from about 200 nm to about 700 nm;
- simultaneous with the step of irradiating the sample, detecting synchronous fluorescence spectra from the sample over a band extending from about 200 nm to 700 nm, the emission wavelength being maintained at a wavelength offset from the excitation wavelength by a fixed amount while scanning the bands, the fixed amount being between about 10 nm and 70 nm;
- identifying and measuring fluorescence intensity maxima in the emission band corresponding to species of porphyrin, bile components, background sample media, tyrosine, tryptophan, NAD(P)H, and flavins; and
- comparing relative concentrations of the species of porphyrins, bile components, background sample media, tryptophan, tyrosine, NAD(P)H, and flavins in order to diagnose cancer condition in a subject from whom the sample is taken.

20. The method for optical analysis of body fluids according to claim 19, wherein said step of irradiating the body fluid comprises irradiating a sample of blood plasma.

\* \* \* \* \*